(12) United States Patent
Kung et al.

(10) Patent No.: US 6,626,821 B1
(45) Date of Patent: Sep. 30, 2003

(54) FLOW-BALANCED CARDIAC WRAP

(75) Inventors: Robert T. V. Kung, Andover, MA (US); Michael T. Milbocker, Holliston, MA (US)

(73) Assignee: ABIOMED, Inc., Danvers, MA (US)

( * ) Notice: Subject to any disclaimer, the term of this patent is extended or adjusted under 35 U.S.C. 154(b) by 0 days.

(21) Appl. No.: 09/863,887

(22) Filed: May 22, 2001

(51) Int. Cl.$^7$ ................................................. A61M 1/12

(52) U.S. Cl. ........................................................ 600/16

(58) Field of Search ............................ 600/16, 17, 18, 600/37; 601/153

(56) References Cited

U.S. PATENT DOCUMENTS

| | | |
|---|---|---|
| 2,826,193 A | 3/1958 | Vineberg |
| 3,464,322 A | 9/1969 | Pequignot |
| 3,587,567 A | 6/1971 | Schiff |
| 3,613,672 A | 10/1971 | Schiff |
| 3,659,593 A | 5/1972 | Vail |
| 3,674,019 A | 7/1972 | Grant |
| 4,157,713 A | 6/1979 | Clarey |
| 4,340,091 A | 7/1982 | Skelton et al. |
| 4,536,893 A | 8/1985 | Parravicini |
| 4,628,937 A | 12/1986 | Hess et al. |

(List continued on next page.)

FOREIGN PATENT DOCUMENTS

| | | |
|---|---|---|
| EP | 0370931 A1 | 5/1990 |
| FR | 2645739 A1 | 10/1990 |
| GB | 2115287 A | 9/1983 |
| JP | 2271829 | 11/1990 |
| SU | 1009457 A | 7/1983 |
| SU | 1734767 A1 | 5/1992 |
| WO | WO 94/21237 | 9/1994 |
| WO | WO 99/22784 | 5/1999 |

OTHER PUBLICATIONS

Anstadt, George L., Blakemore, W.S., Baue, A.E.. "A New Instrument for Prolonged Mechanical Cardiac Massage." Circulation. 1965. vol. 31 and 32, Supplement II, II–43–II–44. Lippincott Williams & Wilkins.

Vaynblat, Mikhail et al. "Cardiac Binding in Experimental Heart Failure." Ann. Thorac. Surg.. 1997. 64:81–85. Elsevier Science Inc..

Vaynblat, Mikhail et al.. "Caridac Binding in Experimental Heart Failure." Circulation. 1995. 92(8):I–380. Lippincott Williams & Wilkins.

Chekanov, Valeri. "Nonstimulated Cardiomyoplasty Wrap Attenuated the Degree of Left Ventricular Enlargement." Ann. Thorac. Surg. 1994. 57:1684–1685. Elsevier Science Inc..

Kass, David A. et al.. "Reverse Remodeling from Cardiomyoplasty in Human Heart Failure: External Constraint Versus Active Assist." Circulation. 1995. 91(9):2314–2318. Lippincott Wiliams & Wilkins.

Carpentier, A., Chachques J.C.. "Myocardial Substitution with a Stimulated Skeletal Muscle: First Successful Clinical Case." The Lancet. 1985. 1:1267. The Lancet Publishing Group.

(List continued on next page.)

*Primary Examiner*—Scott M. Getzow
(74) *Attorney, Agent, or Firm*—Thomas J. Engellenner; Ronald E. Cahill; Nutter McClennen & Fish LLP

(57) ABSTRACT

A flow-balanced cardiac wrap that assists the right and left ventricles of an affected heart to differing, and adjustable degrees is provided. The wrap generally applies an assist to the left ventricle that is greater than that applied to the right, or that reduces blood output from the right relative to the left. In one embodiment, the wrap comprises a material covering that is applied around the right and left ventricles of the heart, so that the left ventricle is assisted over a larger surface area than the right. The positioning of the right ventricular portion or the wrap is chosen so that desired pumping characteristics for the right ventricle are achieved.

37 Claims, 18 Drawing Sheets

U.S. PATENT DOCUMENTS

| | | |
|---|---|---|
| 4,690,134 A | 9/1987 | Snyders |
| 4,803,744 A | 2/1989 | Peck et al. |
| 4,827,932 A | 5/1989 | Ideker et al. |
| 4,902,291 A | 2/1990 | Kolff |
| 4,936,857 A | 6/1990 | Kulik |
| 4,957,477 A | 9/1990 | Lundback |
| 5,078,134 A | 1/1992 | Heilman et al. |
| 5,098,369 A | 3/1992 | Heilman et al. |
| 5,111,818 A | 5/1992 | Suzuki et al. |
| 5,119,804 A | 6/1992 | Anstadt |
| 5,131,905 A | 7/1992 | Grooters |
| 5,169,381 A | 12/1992 | Snyders |
| 5,243,723 A | 9/1993 | Cotner et al. |
| 5,336,254 A | 8/1994 | Brennen et al. |
| 5,383,840 A | 1/1995 | Heilman et al. |
| 5,534,024 A | 7/1996 | Rogers et al. |
| 5,558,617 A | 9/1996 | Heilman et al. |
| 5,564,142 A | 10/1996 | Liu |
| 5,611,085 A | 3/1997 | Rasmussen |
| 5,702,343 A | 12/1997 | Alferness |
| 5,704,891 A | 1/1998 | Mussivand |
| 5,707,336 A | 1/1998 | Rubin |
| 5,713,954 A | 2/1998 | Rosenberg et al. |
| 5,741,316 A | 4/1998 | Chen et al. |
| 5,800,528 A | 9/1998 | Lederman et al. |
| 5,853,005 A | 12/1998 | Scanlon |
| 5,902,229 A | 5/1999 | Tsitlik et al. |
| 5,971,910 A | 10/1999 | Tsitlik et al. |
| 5,991,665 A | 11/1999 | Wang et al. |
| 5,991,925 A | 11/1999 | Wu |
| 6,065,154 A | 5/2000 | Hulings et al. |
| 6,076,013 A | 6/2000 | Brennan et al. |
| 6,179,793 B1 | 1/2001 | Rothman et al. |
| 6,179,800 B1 | 1/2001 | Torrens |
| 6,212,430 B1 | 4/2001 | Kung |
| 6,221,103 B1 | 4/2001 | Melvin |

OTHER PUBLICATIONS

Anstadt, Mark P., Anstadt, George L., Lowe, James.. "Direct Mechanical Ventricular Actuation: A Reveiw." Resuscitation. 1991. 21:7–23. Elsevier Science Inc..

Anstadt, Mark P., Stonningham. Michael J., Tedder, Mard, Crain, Barbara J., Menius, J. Alan, Lowe, James E.. "Pulsatile Reperfusion After Cardiac Arrest Improves Neurologic Outcome." Annals of Surgery 1991. 214(4):478–490. American Surgical Association.

Bencini, Adriano., Parola, Pier L.. "The 'Pneumomassage' of the Heart." Surgery. 1956. 39:375–384.The National Medical Society.

Capouya, Eli R. et al.. "Girdling Effect of Nonstimulated Cardiomyoplasty on Left Ventricular Function." Ann. Thorac. Surg. 1993. 56:867–71. Elsevier Science Inc..

Carpentier, Alain et al.. "Dynamic Cardiomyoplasty at Seven Years." The Journal of Thoracic and Cardiovascular Surgery. 1993. 106(1):42–54. Mosby, Inc.

Article "Tissue Engineering" Robert Langer and Joseph P. Vancanti; Science, vol. 260, May 14, 1993; pp. 920–926.

Article "Biodegradable Polymer Scaffolds for Tissue Engineering" Lisa E. Freed; Gordan Vanjak–Novakovic; Robert J. Biron; Dana B. Eagles; Daniel C. Lesnoy; Sandra K. Barlow and Robert Langer; Bio/Technology vol. 12, Jul. 1994; pp. 689–693.

U.S. patent application Ser. No. 09/661,624, Milbocker, et al., filed Sep. 14, 2000.

FLOW-BALANCED CARDIAC WRAP

RELATED APPLICATIONS

This application is related to commonly owned U.S. patent application Ser. No. 09/661,624 entitled SYSTEM AND METHOD FOR IMPLANTING A CARDIAC WRAP, by Michael T. Milbocker et al and commonly owned U.S. patent application Ser. No. 09/877,055 entitled EXTRA-CARDIAC ASSIST DEVICE WITH INTERNAL INFLATION PATH by Robert T. V. Kung et al, the teachings of which patent applications are all expressly i orated herein by reference. This application is also related to U.S. Pat. No. 5,713,954 and U.S. Pat. No. 5,800,528, both expressly incorporated herein by reference.

BACKGROUND OF THE INVENTION

1. Field of the Invention

This invention relates to extra-cardiac assist devices and more particularly to cardiac wraps that are selectively inflated and deflated to cyclically apply pressure to a treated heart.

2. Background Information

Ventricular enlargement is a clinically dangerous condition in which a ventricle of the patient's heart increases in radius (e.g. dilates) until it is incapable of adequately pumping necessary blood through the patient's body. Other equally life-threatening heart failure conditions may also result from severe heart attacks, with rapid deterioration of blood-pumping cap ability of the heart. A number of invasive procedures have been employed through the years in an effort to remedy ventricular dysfunction resulting from progressive acute conditions. Many of these procedures involve the use of cardiac assist devices that are implanted through the wall of the heart, and thereby come into direct contact with the bloodstream and internal vascular tissue. One potential disadvantage of such internally implanted devices is a chronic stimulus for blood clots or thrombosis and possible thromboembolism. This stimulus is present whenever artificial materials come in contact with blood, causing the accretion thereon of blood components. Thrombogenesis is typically controlled, or at least reduced through anticoagulation therapy. Such anticoagulants have several undesirable side effects, such as a higher propensity for bleeding.

Improved therapies and associated devices now exist that, under certain conditions, can replace internally implanted blood pumps. Ventricular dilation can be effectively treated using implants that are essentially free of contact with the heart's internal, blood-contacting surfaces. U.S. Pat. No. 5,800,528, entitled PASSIVE GIRDLE FOR HEART VENTRICLE FOR THERAPEUTIC AID TO PATIENTS HAVING VENTRICULAR DILATION by Lederman et al., expressly incorporated herein by reference, teaches one such treatment device. The device is applied over the affected ventricle or both affected ventricles by the clinician/surgeon, and held in place by small internal hooks (microhooks) or other fastening devices (sutures) that engage the outer wall of the heart. The girdle can be further constricted to better fit or compress the dilated ventricle using various mechanical systems such as pneumatic/hydraulic balloons or drawstrings. In this manner, the compression of the girdle passively (and continuously) counteracts excessive dilation of the ventricle.

U.S. Pat. No. 5,713,954, entitled EXTRA-CARDIAC VENTRICULAR ASSIST DEVICE by Rosenberg et al., also expressly incorporated herein by reference, teaches an active device that dynamically assists in the pumping of blood by the ventricles. Such an active device can treat both progressive and acutely failing heart conditions. This device is, like the girdle, placed around the affected ventricles and secured. A hydraulic or pneumatic (e.g. fluid) control system enables internal inflation elements (balloons) within the device to repetitively inflate and deflate, respectively squeezing and allowing expansion of the ventricle.

Both of the above-described exemplary devices employ an element termed a "wrap" that essentially wraps around the ventricular region of the heart. Active wraps inflate and deflate cyclically to assist the heart in the pumping of blood and may have a variety of shapes and sizes. They can be tailored to fit a particular affected heart, and accordingly, to operate to best treat the underlying condition of that heart.

The active extra-cardiac assist devices described above apply fluid-driven dynamic forces to expel blood from the ventricles of a heart. The forces are derived from either pneumatic or hydraulic actuation of the inflation elements so as to either apply the inflation pressure directly to the epicardium of the affected heart, or transduce the inflation pressure into a circumferential contraction about the heart. Devices operating under the former direct application principle are known as displacement devices, and generate maximally one unit of stroke volume in the heart for each corresponding unit of inflation volume. Devices operating under a contractile principle are not so limited, and in practice can achieve a relative gain in stroke volume in the heart of three to four times the inflation volume of the device. Because they require less volume, contractile devices also offer the opportunity for total device implantation. Displacement devices are powered by an extra-corporeal pressure/vacuum source.

In general, the self-contained balloons of the inflation elements are formed of a fatigue-resistant, biocompatible substance such as polyurethane. The inflation elements are located in pockets formed between a pair of fabric layers. A biocompatible fabric, such as woven polytetrafluoroethylene (PTFE) can be used. Pockets are defined by, for example, sewn seams. The seams typically consist of a strong, multifilament thread, formed from a biocompatible material such as Dupont Tyvek®, that bridges or joins the above-mentioned biocompatible fabric. The fabric can be covered with a polymer or lightweight silicone coating to render it impermeable to fluid and tissue.

When a cardiac wrap is applied to an affected heart, it may enclose both the left and right ventricles to a large degree, applying a fixed or dynamic pressure to both simultaneously. However the afterload pressures (e.g. the pressure to eject blood from the ventricle) required in the right and left ventricles are not the same. The right ventricle exhibits a lower afterload pressure (approximately 20 mm/Hg) than that of the left ventricle (approximately 100 mm/Hg). Pressure applied to the whole ventricular surface (left and right) generally causes the right ventricle to empty first. In the case in which the left ventricle pumps less blood than the amount of blood entering the right ventricle, pulmonary edema results. Difference between right ventricular output and left ventricular output is balanced in the normal heart through the bronchial shunt, and by various changes in ventricular contractility based upon various neuro-hormonal feedback mechanisms. However, in unhealthy hearts, this balance may not be maintained, and needs to be provided for by a heart, assist device.

A number of current displacement and contractile cardiac wrap designs apply pressure to both ventricles simultaneously. The coverage area of these wraps for each of the left and right ventricles is roughly the same. However, the right ventricle pumps against significantly less afterload pressure to eject blood than the left ventricle due to the direct, low-resistance flow path from the right ventricle to the left ventricle via the pulmonary artery (compared to the aortic flow path serviced by the left ventricle. Therefore, the amount of applied contraction or displacement (for active wraps) to the right ventricle always occurs before the left ventricle is affected. In summary, existing wrap designs, that provide somewhat uniform pumping action across both the left and right ventricles, may over-pump the right ventricle in an effort to provide sufficient pumping action to the left ventricle, thereby defeating the balancing effect of the bronchial shunt. This can cause elevated right ventricular afterload, thereby increasing the threat of pulmonary edema.

It is therefore an object of this invention to provide a flow-balanced cardiac wrap in which right ventricular and left ventricular outputs are adjusted in order to prevent pulmonary edema or a worsening of ventricular function. Where the cardiac wrap is a permanent or semipermanent implantation, its inflation geometry should generally minimize the likelihood of bacterial colonization. The wrap should also provide improved fit and serviceability when applied to the affected heart.

SUMMARY OF THE INVENTION

This invention overcomes the disadvantages of the prior art by providing a flow-balanced cardiac wrap that assists the right and left ventricles of an affected heart to differing, and adjustable degrees. The wrap generally applies an assist to the left ventricle that is greater than that applied to the right, or that enables higher blood output from the left with respect to the right.

In one embodiment, the wrap comprises a material covering that is applied around the right and left ventricles of the heart, so that the left ventricle is assisted over a larger surface area than the right. The positioning of the right ventricular section of the wrap is chosen so that desired pumping characteristics for the right ventricle are achieved. For example, the positioning can be chosen to block a predetermined amount of blood flow within the right ventricle from reaching the heart valve and pulmonary artery. The wrap can include a pair of free ends with adjustable closures/connectors that are brought into engagement during implantation to complete the enclosure around the heart. The connectors can be arranged to enable selective placement of the right ventricular section. The wrap can be generally adapted to include adjustment elements, such as ties that allow the cone angle of the wrap with respect to the heart to be varied.

The wrap can include inflation elements positioned between material layers on the wrap to provide active assistance to the pumping action of the ventricles based upon the direction of fluid into the inflation elements. The placement, size and number of inflation elements can be varied relative to the left and right ventricular sections of the wrap. In addition, the pump and fluid interconnections can be adapted to provide different volumes of inflation fluid to each section, to deliver fluid at different flow rates, and/or to trigger inflation at different times. The inflation/deflation times can be set so that systole is held, and deflation of the overall wrap structure is delayed, with respect to the heart's natural rhythm. The left ventricle can be displaced before the right and vice versa. Attentively, the right ventricle can be displaced every two cycles (e.g. every other cycle) with respect to displacement of the left ventricle.

According to another embodiment, the wrap can include dead spaces or semi-rigid members to alter the pressure-application characteristics of the wrap at certain locations. In yet another embodiment, the inflation elements can be moved about the circumference of a non-distensible wrap cover to apply selective displacement at different locations on the wrap.

BRIEF DESCRIPTION OF THE DRAWINGS

The foregoing and other objects and advantages of the invention will become clearer with reference to the following detailed description as illustrated by the drawings, in which.

DETAILED DESCRIPTION OF AN ILLUSTRATIVE EMBODIMENT

Figure 1:
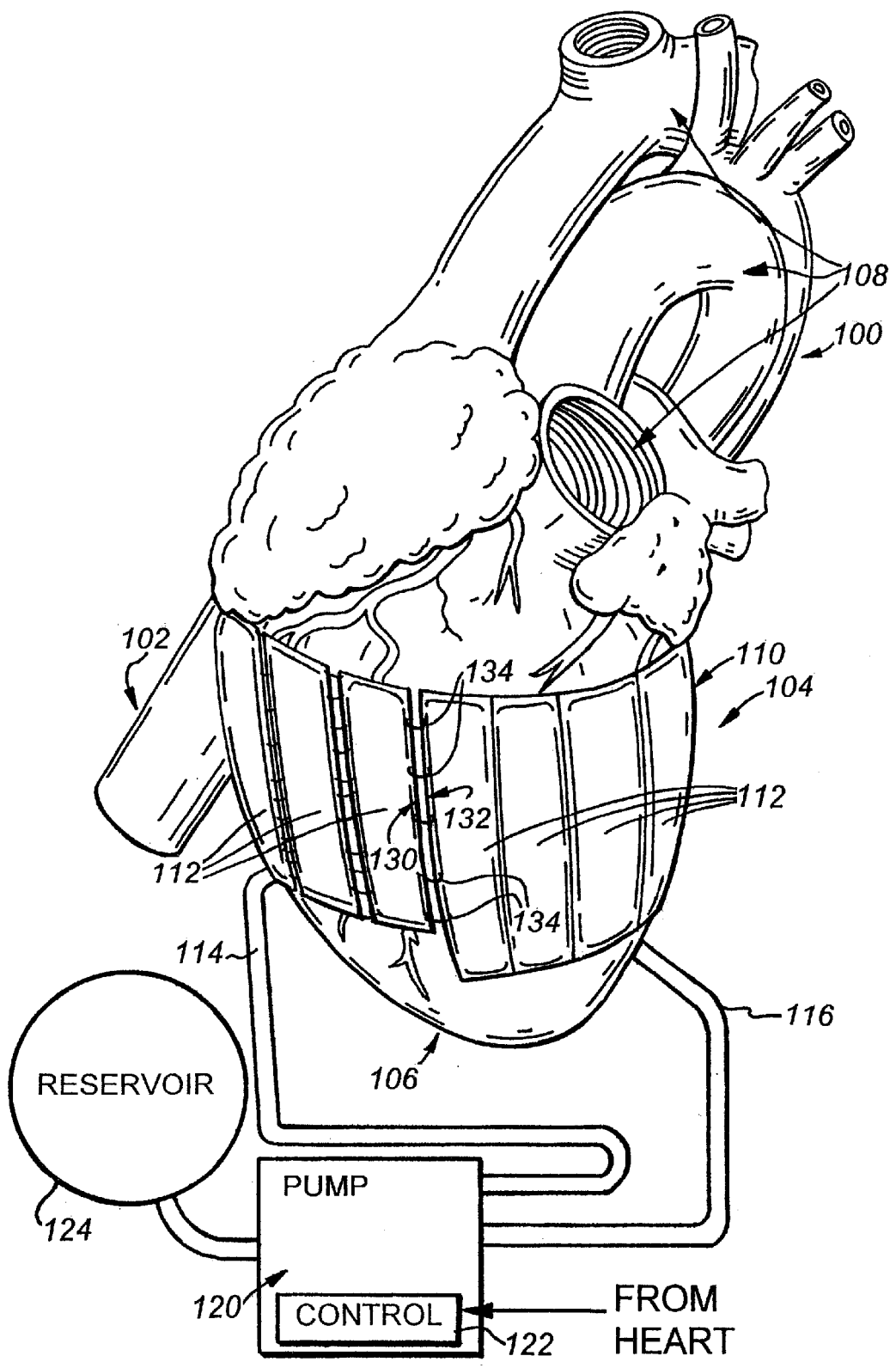
FIG. 1 is a perspective view of an affected heart having a flow-balanced cardiac wrap according to an embodiment of this invention applied thereto.

FIG. 1 shows a heart 100 suffering from ventricular dysfunction. The heart includes a right ventricular region 102 and left ventricular region 104, an apex 106, and major blood vessels 108. Note that, as used herein, the terms "right" and "left" refer to the standard anatomical reference for the right and left ventricles—and therefore are reversed from the depicted orientations. Applied to the heart is an extra-cardiac assist device—cardiac wrap 110 that encloses selected portions of the ventricular region 102, 104. The wrap 110 can include a series of distensible tubes or balloons termed generally as inflation elements 112 herein. The inflation elements 112 are arranged in parallel (longitudinally) in this embodiment receive inflation fluid (gas or liquid) via external tubular feed conduits 114 and 116 (two conduits in this example). The conduits 114, 116 can feed the individual inflation elements by employing an interconnected fluid distribution network that interconnects the various inflation elements. The distribution network can be internal to the wrap. With particular reference to FIG. 1, the network is obscured by the wrap. Alternatively, the distribution network can be external to the body of the wrap using a variety of techniques discussed in further detail in the above-incorporated Milbocker, et al document. The conduits 114, 116 are fed by a pump unit 120 having a control mechanism 122 that can include various mechanical and electronic sensors and regulating components. The control 122 can receive inputs from a variety of heart sensors and monitors that sense and analyze the heart's function, rhythm, etc. This is described further below. The pump includes a reservoir 124 for storing return fluid between inflation cycles. The pump 120, reservoir 124 and any associated power source can be variously mounted within the patient's body or externalized. The wrap can be attached and secured to the heart using a variety of techniques including microhooks that grasp the heart wall or sutures. The wrap is typically applied to the heart with free ends 130, 132 unsecured, and these ends are then brought into engagement to customize fit, location and orientation. Sutures or ties 134 can be employed to secure the ends—or a variety of other securing mechanisms can be used, as described in detail below.

Figure 2:
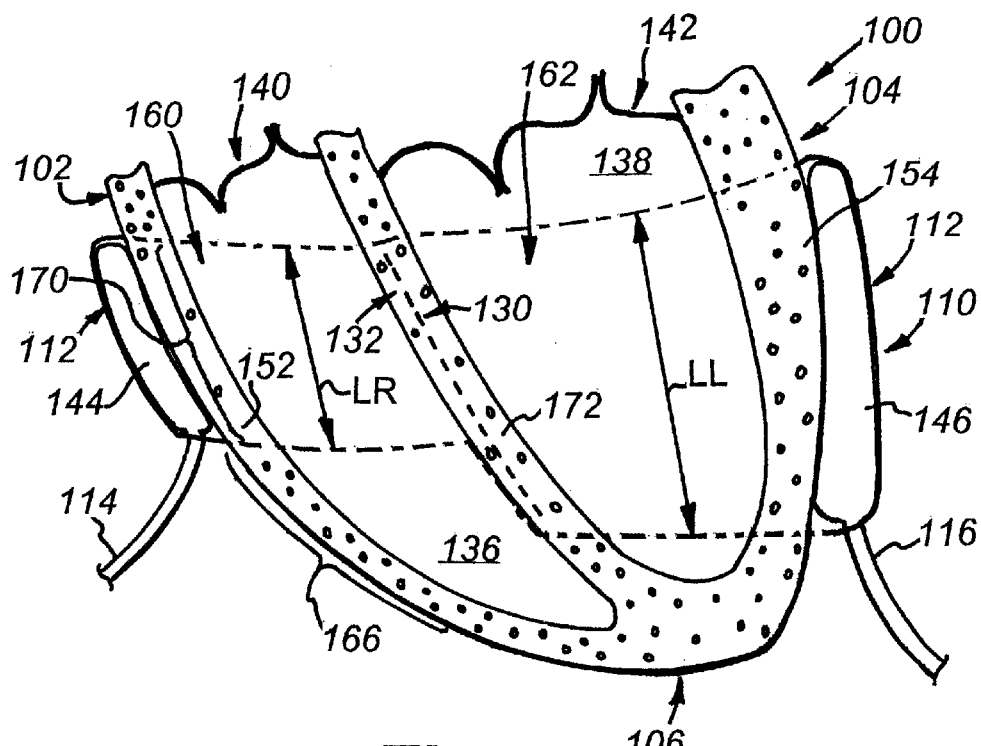
FIG. 2 is a side cross section of the right and left ventricular region of the heart with the flow-balanced cardiac wrap of FIG. 1 applied.

Referring also to FIG. 2, the fit and internal structure of the wrap 110 is shown in further detail. The ventricular region of the heart 100 is revealed in cross section. The right ventricle 136 and left ventricle 138 are shown. Also shown are the heart valves 140 and 142 (schematically) in the region of the atrio-ventricular (AV) groove. Note that inflation elements 112, according to an embodiment of this invention, are also shown in cross section. These elements 112 include balloons 144 and 146. These balloons can be constructed as separate sealed members within a separate fabric/sheet-material structure, or the inflation elements can be unitary members formed by opposing fluid-impermeable wrap layers (refer to the incorporated Milbocker document above). The balloons in this embodiment are separate units residing within discrete pockets in the wrap material. The balloons 144, 146 are inflatable tubes constructed from thin-walled polyurethane (10-mil-thickness in this example), that are in fluid communication with respective conduits 114, 116. The inflatable wraps described herein can be designed to inflate and deflate according to a diastolic and systolic pumping cycle, or can be adapted to remain at a given, fixed displacement,pressure until readjusted. The depicted embodiment now described provides a continuous cyclical pumping action.

The wrap 110 (which can be either a displacement-type or contractile-type) applies a pressure to the fight and left ventricular free walls 152, 154 through inflation of the balloons, thereby providing direct displacement or transduced circumferential contraction force applied to the ventricular free walls. The wrap may consist of a single enclosed volume. The right ventricular free wall 152 and left ventricular free wall 154 are shown in relation to the wrap 110. In this embodiment, the right portion 160 of the wrap covers and applies pressure to an assisted portion of the right ventricular free wall 152. Similarly the left portion 162 covers and applies pressure to the left ventricular free wall 154.

In extra-cardiac assistance, the output imbalance between the right ventricle 136 and the left ventricle 138 is due to excess output from the right ventricle as a result of the lower afterload condition. One approach to reducing right ventricular output during assistance is to reduce the area of the particular cardiac free wall receiving pressure from the cardiac assist device. For this reason, the area of the right ventricular free wall 152 covered by the right wrap portion 160 is less than the area of the left free wall 154 covered by the left wrap portion 162. There is, therefore, a section 166 of the right ventricular free wall 152, which is not in contact with the wrap 110, and is not assisted. In one embodiment, the length LR of the right portion 160 can be approximately 1 inch, while the length of the left portion LL is approximately 1-2 inches. However these length measurements can vary.

Figure 3:
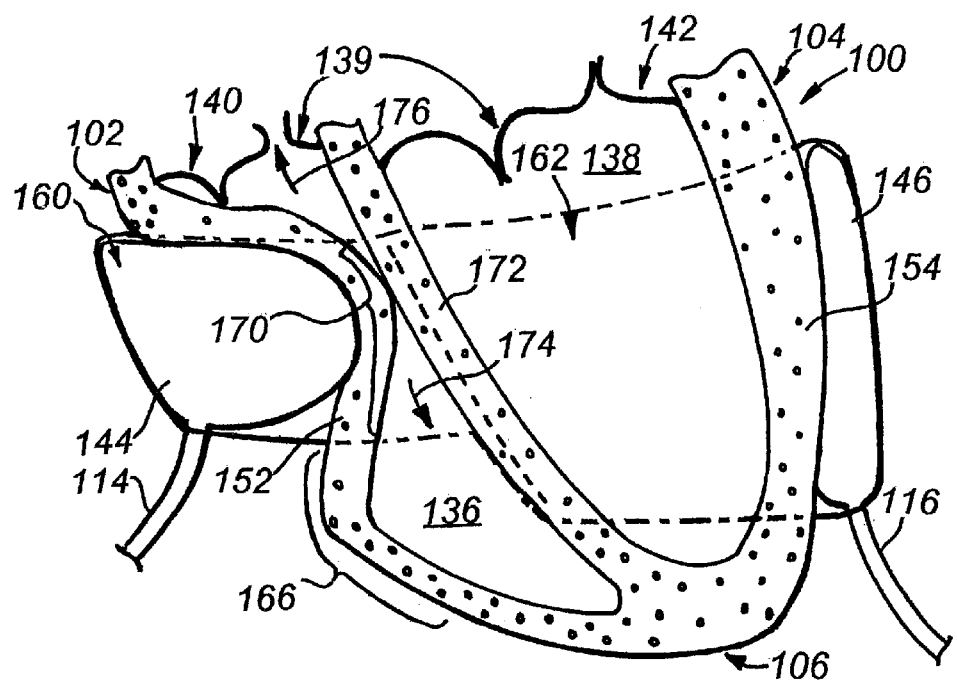
FIG. 3 is a side cross section of the heart ventricles and cardiac wrap of FIG. 2 showing initial inflation of the right ventricular region.

As part of the operation of the wrap 110 of this embodiment, as a result of the smaller volume on the right side, which expedites right inflation for a given amount of fluid pumped, the right side inflation tends to lead the left. In addition, the pump can be adapted to control inflation of the right portion 160 so that it leads the inflation of the left portion 162, using the control 122 (FIG. 1). As shown in FIG. 3, when the initial inflation of the wrap 110 causes the covered portion 170 of the right ventricular free wall 152 to collapse toward the interventricular septum 172, causing a certain volume of the total blood volume within the right ventricle 136 to be displaced from the covered portion 170. The displaced blood flows (arrow 174) partially toward the uncovered right free wall section 166 near the apex 106, where it is prevented from reaching the heart valve plane 139. The remaining displaced blood flows (arrow 176) toward, and through, the heart valve 140.

Figure 4:
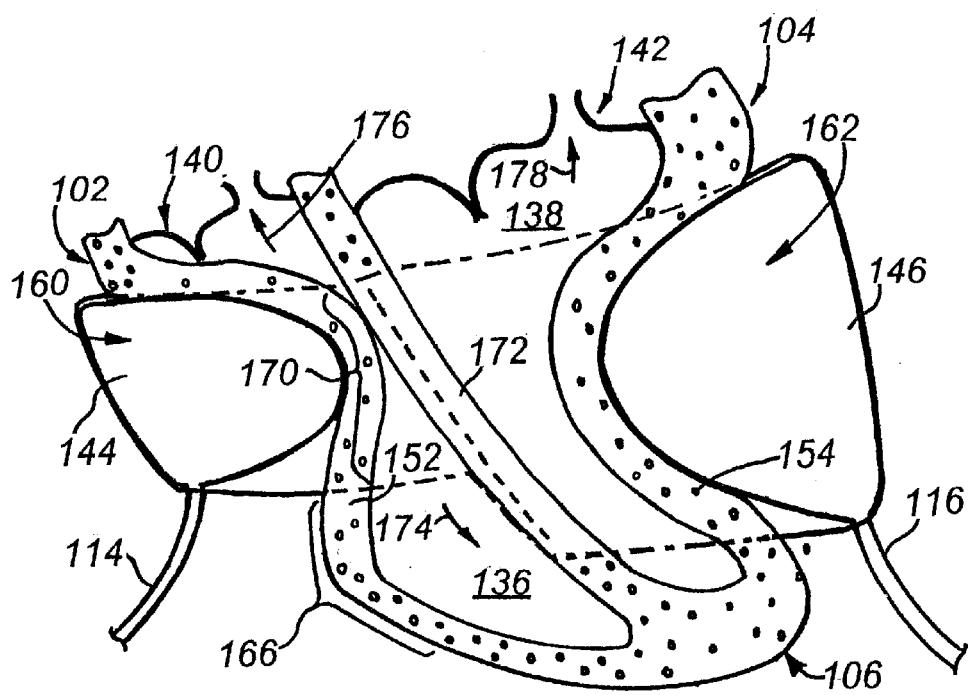
FIG. 4 is a side cross section of the heart ventricles and cardiac wrap of FIG. 3 showing continuing inflation of the left ventricular region.

As the overall pressure in the wrap 110 increases during inflation, the left ventricular free wall 154 is also compressed as depicted in FIG. 4. This causes ejection of a required volume of blood in the left ventricle 138 through the valve 142 (arrow 178). Meanwhile, the reduced volume allowed to exit from the right ventricle 136 prevents overload of pulmonary blood vessels.

Figure 5:
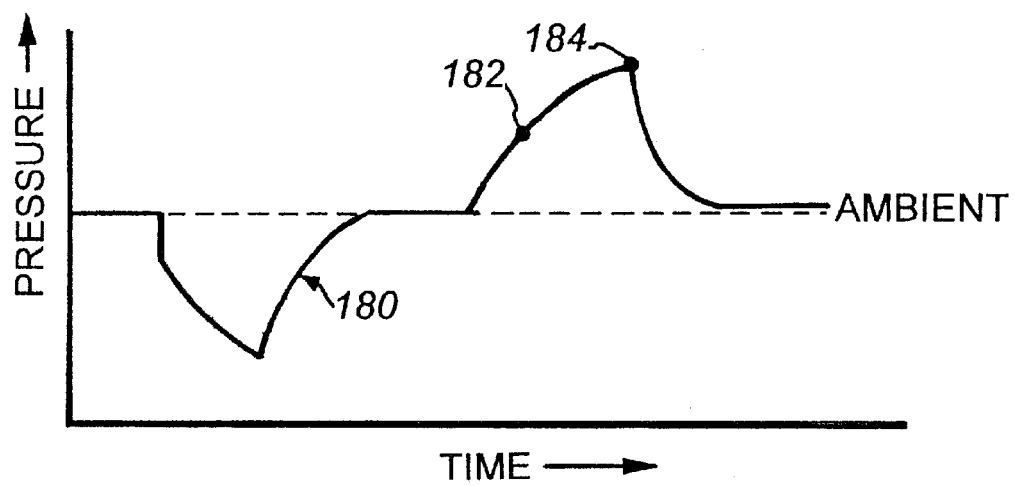
FIG. 5 is a graph of internal cardiac wrap pressure versus time.

For purposes of further illustration, FIG. 5 is a graph of internal wrap pressure 180 (with respect to the normal ambient pressure) versus time. Graph point 182 indicates collapse of the right ventricle 136 as depicted in FIG. 3, and graph point 184 indicates collapse of the left ventricle 138 as depicted in FIG. 4. By varying area of the covered portion 170 with respect to the uncovered portion 166, the volume of blood ejected out of the right ventricle can be readily adjusted relative to ejection volume from the left ventricle.

Figure 6:
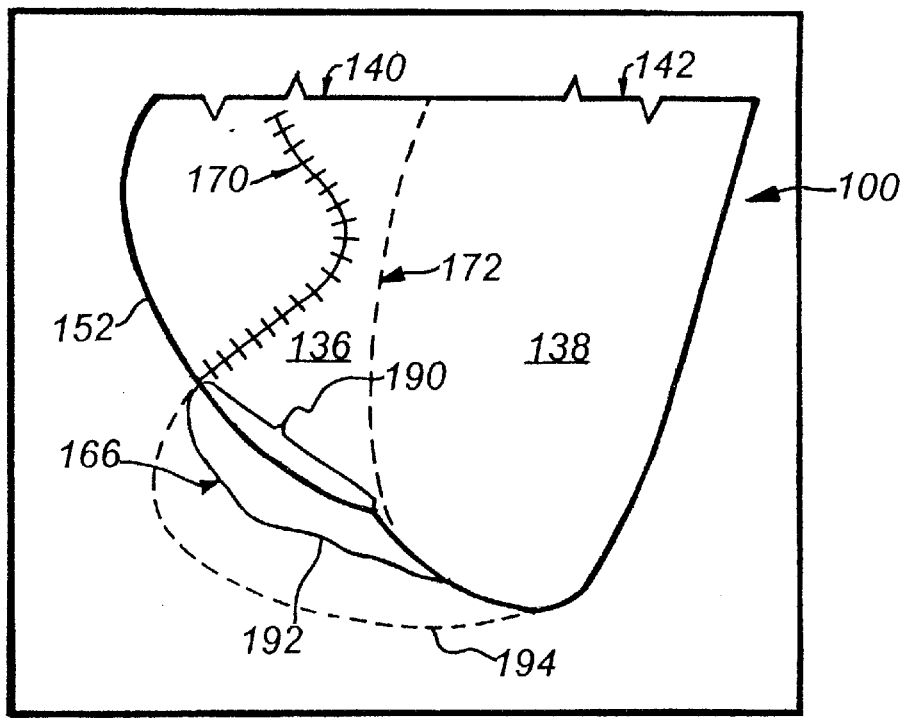
FIG. 6 is a schematic side cross section of the right and left ventricular region of the heart showing dilation in the right ventricular free wall under certain conditions.

For certain pathological heart conditions, the uncovered portion 166 of the right ventricle may tend to dilate beyond the normal end diastolic position. FIG. 6 schematically illustrates the unassisted end systolic position (190) of the uncovered portion of the right ventricular free wall 152. The desired end systolic position (192) of the uncovered portion 166 right ventricular free wall is also shown. Assistance of the right ventricle can cause to uncovered portion 166 of the right ventricular free wall to eventually deform into a further dilated shape that extends beyond the end systolic position (190). The effect of this condition may be to weaken or cause to fail the right ventricle 136. In addition, this condition may create an increasing condition of imbalance between right and left ventricular blood flows as the uncovered portion of the right ventricular free wall continues to dilate further over time into a chronic dilated position (194).

FIG, 7 details a wrap 200 that alleviates the risk of excessive dilation in the uncovered right-ventricular portion 166. A non-distensible, non-inflating wall extension 202 is joined to the inflating right wrap section 204. This extension 202 can extend from the lower edge 208 of the wrap to a boundary line 210 adjacent to the apex 106. It can be constructed from a fabric or non-distensible/strongly elastic material shaped to conform to the portion 166. The boundary can be aligned generally with the bottom edge of the left wrap section 212 in one embodiment. The wall extension 202 prevents outward dilation of the portion 166, but does not exert displacement pressure, thereby restraining the portion 166 near or at the nominal end diastolic position. Note that the wall extension 202 can provide a slight, fixed inward displacement of the portion 166 to reduce right ventricle volume and ensure that little or no dilation occurs.

Figure 7:
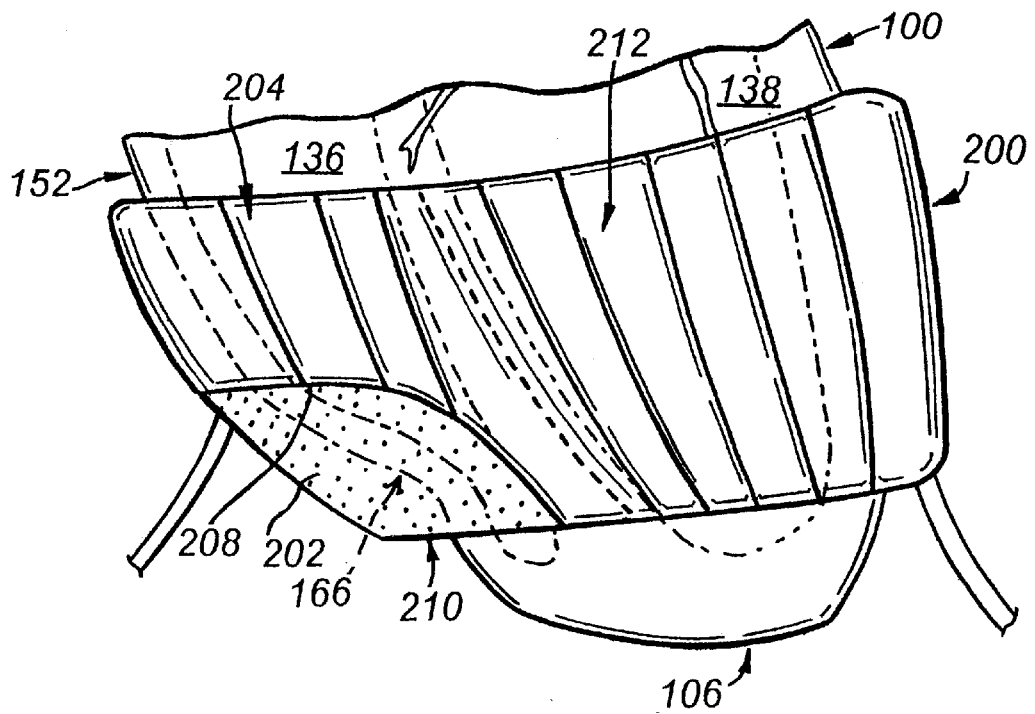
FIG. 7 is a partially exposed side view of the right and left ventricular region of the heart with cardiac wrap applied thereto having a non-distensible wall extension.
Figure 8:
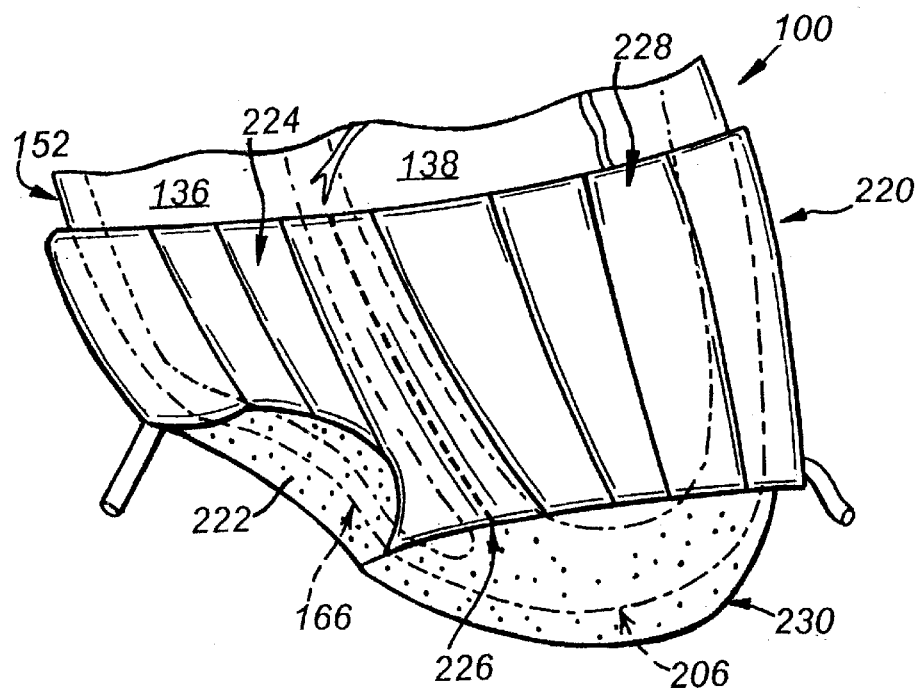
FIG. 8 is a partially exposed side view of the right and left ventricular region of the heart with applied cardiac wrap of FIG. 7 including an additional enclosure around the heart apex.

FIG. 8 details an alternate embodiment of a wrap 220 that further controls potential dilation of the right ventricular free wall portion 166. The non-distensible wall extension 222 is attached beneath the right wrap portion 224 as described generally above (refer to FIG. 7). The wall extension 222 extends to, and is aligned with the lower edge 226 of the left wrap portion 228. Attached to the lower edge 226, about the entire circumference is a further piece of non-distensible material covering 230. This covering joins the wrap around the heart apex 106, and serves to further restrain the right ventricular free wall, as well as the septal plane, from undesired dilation. It is expressly contemplated that an appropriate adaptation of the wall extension 222 and/or apex covering 230 can be applied to any of the wrap designs described herein.

Figure 9:
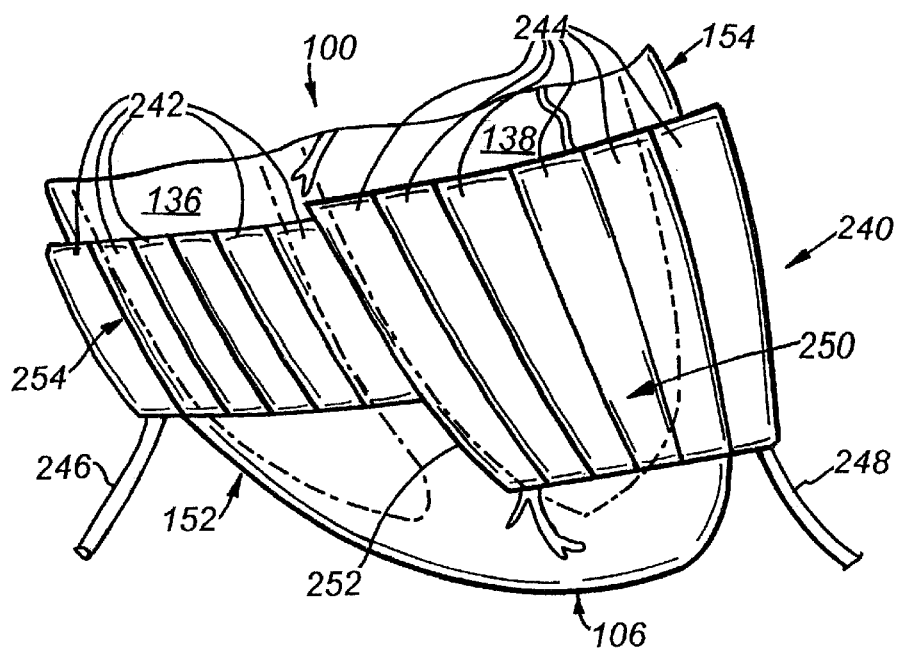
FIG. 9 is a partially exposed side view of the left and right ventricular region of an affected heart with applied cardiac wrap having contractile members.

According to an alternate embodiment, the principle of partial ventricular assistance as described generally above can be adapted more particularly to contractile wraps, such as that described in the above-incorporated U.S. Pat. No. 5,713,954 by Rosenberg et al. FIG. 9 shows a contractile wrap 240 applied to the affected heart 100. The wrap is constructed with contractile tubes 242 and 244 that cause the inner circumference of the wrap 240 to decrease in response to fluid flow into the conduits 246 and 248 from the pump (not shown). The left ventricular free wall 154 is covered by an elongated wrap section 250. This section is joined along its edge 252 with the shortened wrap section 254 that engages the middle region of the right ventricular free wall 252. The effect of contraction of the right wrap portion 254 on the right ventricle (e.g. reduced flow to the pulmonary artery) is generally the same as described comprehensively above for displacement and contractile wraps.

Figure 10:
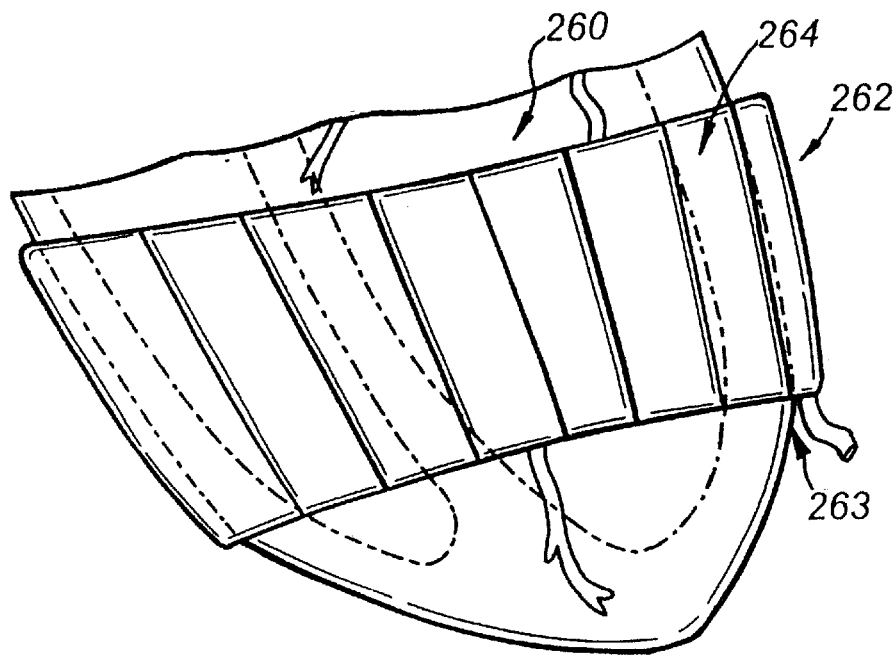
FIG. 10 is a partially side view of the left and right ventricular region of an affected heart with applied cardiac wrap for providing partial assistance to the left ventricle.

According to another alternate embodiment, shown in FIG. 10, a wrap 262 provides approximately equal assistance to the left ventricular free wall 263 and the right ventricular free wall using an appropriately sized left wrap section 264.

Figure 11:
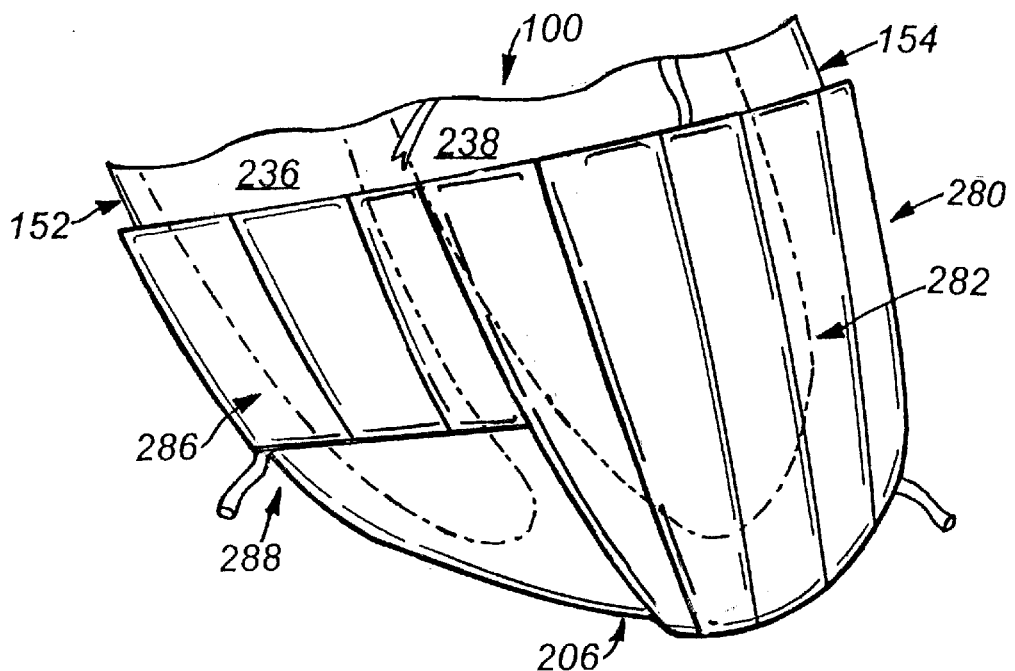
FIGS. 11–13 are partially exposed side views of the left and right ventricular regions of an affected heart showing cardiac wraps that exhibit a variety of configurations with respect to the ventricles.

The principle of partial ventricular assistance described above is effective in a variety of configurations. FIG. 11 depicts a wrap 280 having a left section 282 for fully assisting the left ventricle 238 and a right section 286 that actuates the right ventricular free wall 152 adjacent to the free wall base position 288.

Figure 12:
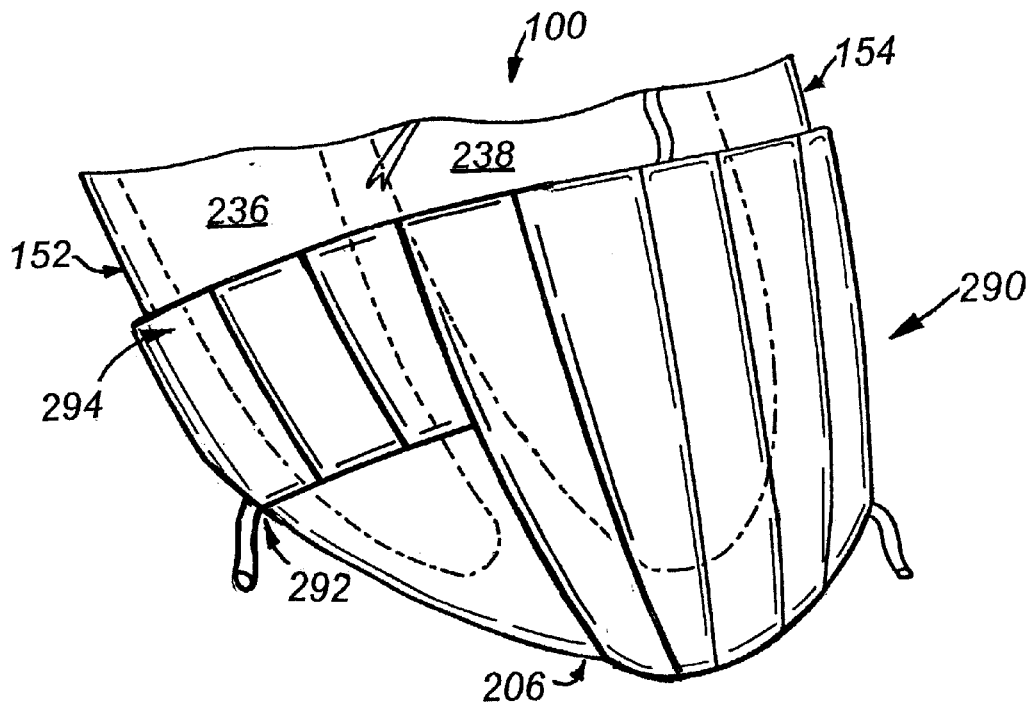
Figure 13:
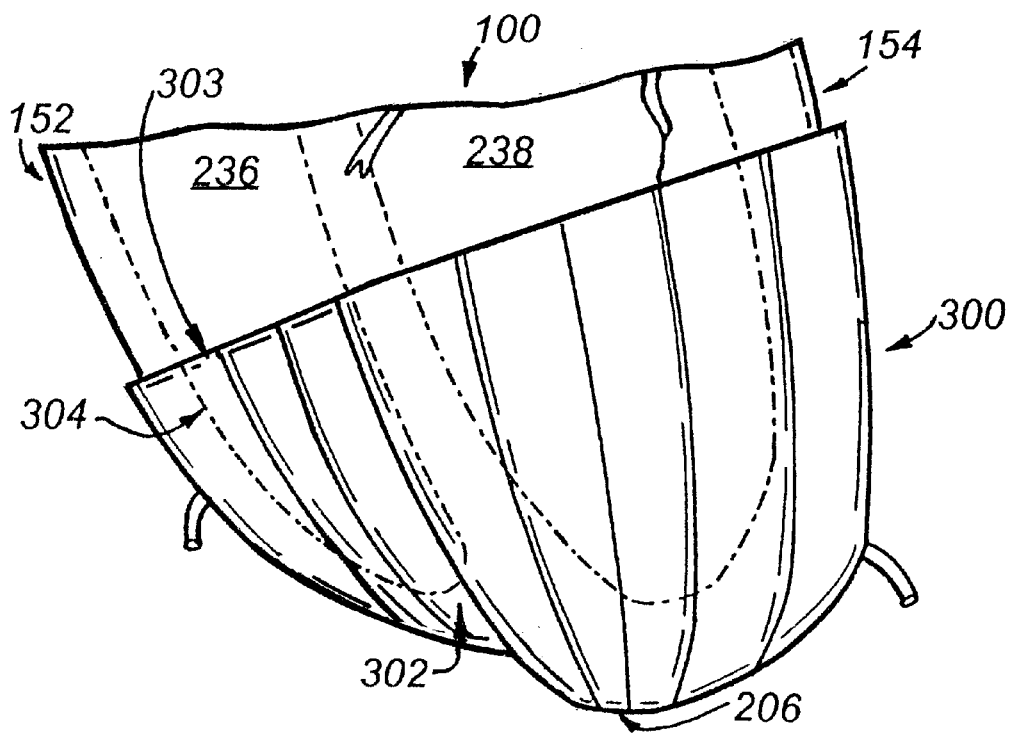

Similarly, FIG. 12 depicts a wrap 290 actuating the mid-free wall 292 with right wrap portion 294. Also, FIG. 13 depicts a wrap 300 that actuates the apical free wall 302 (adjacent to heart apex 206). Note that the upper edge 303 of the right section 304 of the wrap 300 is positioned lower on the right ventricular free wall as a result of the apical bias.

Figure 14:
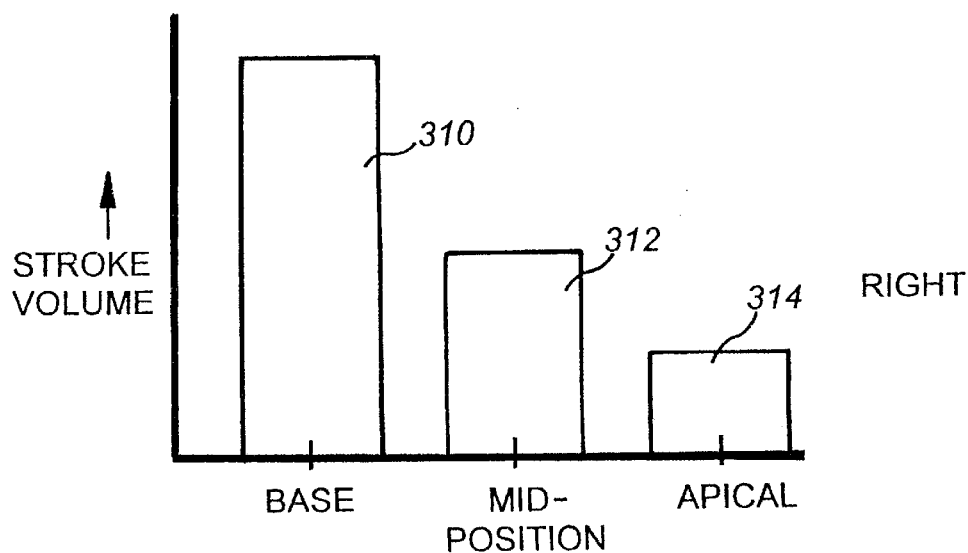
FIG. 14 is a bar graph of right ventricular ejection volume versus ventricular positional location: for equal areas covered by the cardiac wrap.

FIG. 14 is a bar graph comparing the relative stroke (blood ejection) volume for three right wrap sections placed at the base position (310), mid-wall position (312) and apical position (314), where the respective wall coverage area for each position is essentially equal. The generated stroke volume is greatest at the base position, intermediate at the mid-position, and least at the apical position.

Figure 15:
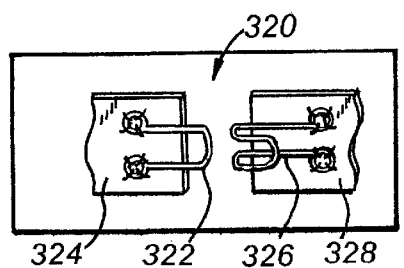
FIGS. 15–18 are fragmentary perspective views of closures for joining free ends of a cardiac wrap to provide for varied positional locations for a section of the wrap with respect to the ventricular region.
Figure 16:
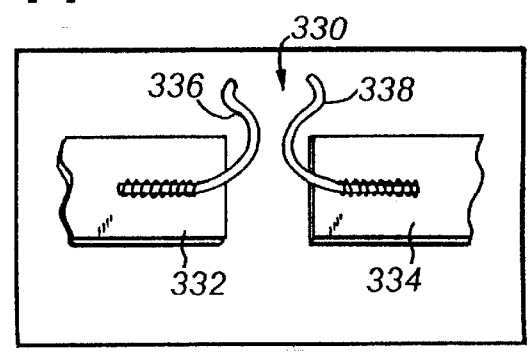

To provide for optimal fit, and variations in the degree of assist, the wrap can be constructed as a modular system. For example, to achieve the configurations depicted in FIGS. 11, 12 and 13, the left and right sections of the wrap may be separate and adapted to be joined in a desired configuration. To accomplish this, each section may include bases at its respective free ends that are adapted to be attached by appropriate joint connectors to the free ends of the other section, thereby defining a readily available closure. FIG. 15 shows an exemplary section connector pair 320 comprising a loop 322 on one section's free end 324 and an interengaging hook 326 on the opposing section's free end 328.

FIG, 16, alternatively, shows a tie closure system, in which each section free end 332 and 334 includes a respective tie 336 and 338. The ties 336, 338 can be brought together and knotted to achieve a desired final circumference for the wrap and appropriate right-versus-left section positioning.

Figure 17:
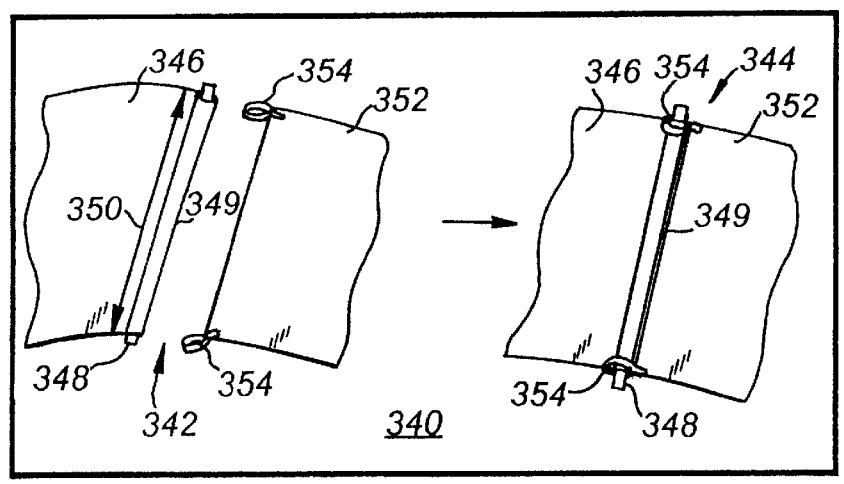

Another closure system 340 is shown in disconnected (342) and connected (344) orientations in FIG. 17. A first section 346 has a rigid or semi-rigid rod 348 captured within a folded-over end 349. The rod extends beyond the width 350 of the section 346. It can be inserted and removed from the folded-over end 349 or permanently mounted. The opposing section 352 includes a pair of end loops 354. The end loops 354 fit over and are retained by the rod 348 in a connected orientation (344). Using a modular approach as number of differently sized and shaped sections can be joined together at mating free ends, allowing standardized components to form a large number of semi-custom wrap arrangements.

Figure 18:
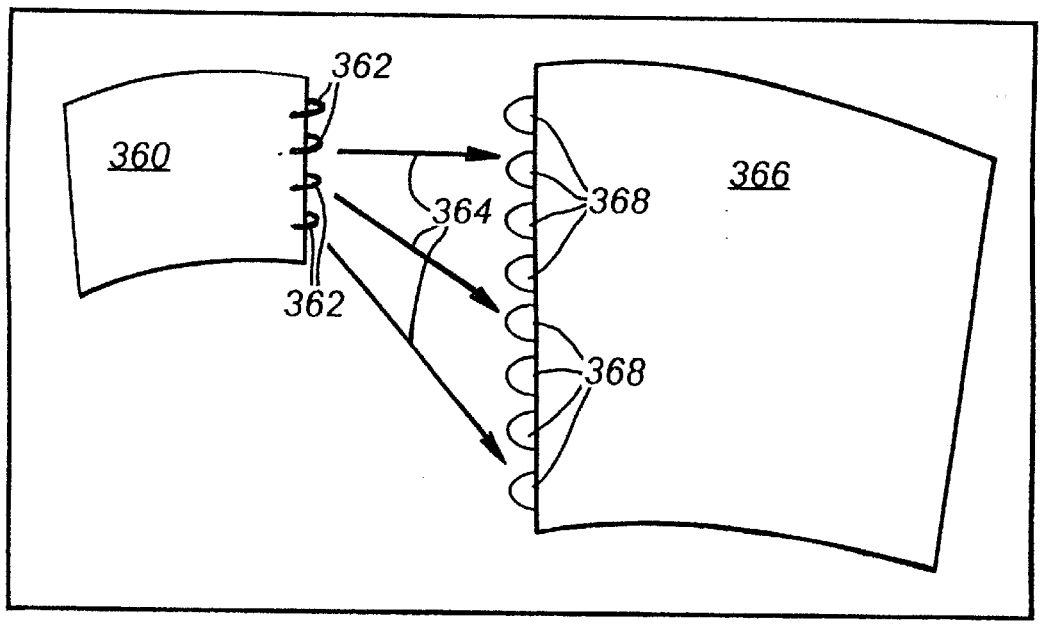

A series of connectors, such as those described above, can be disposed along the free end of each opposing section as shown in FIG. 18. For example the right section 360 has four evenly spaced hooks 362 along its free end. This allows it to be joined in several different configurations (arrows 364) along the opposing free end on the left section 366,which contains twice the number of evenly spaced loops 368 for receiving the hooks 362. In other words, by joining the selected hooks and loops together, the fit and placement of the right section with respect to the left can be altered within a given range that can extend from base to apical as described above. Similar arrangements (e.g. multiple connection positions) cane provided by employing a variety of alternate fastener system including, but not limited to, ties, rods and loops, snaps and sutures.

The modular approach for connecting wrap sections, described above, can be adapted to any number of variations on wrap design. For example, in contractile wrap designs, the contractility of the wrap decreases as the inflation element circumference decreases for a fixed end inflation pressure. Given that a wrap tends to become fixed to the heart surface over time due to tissue growth thereon, or can be adapted to promote such adhesion through the use of textured surfaces on the wrap, the left and right sides can be functionally decoupled, as the sections will be essentially anchored independently to their respective sides of the heart. In other words, the pressure exerted by the left section primarily affects the left ventricle, to which it is anchored, and the pressure exerted by the right section primarily affects the right ventricle. Using this principle, smaller-circumference inflation elements can be employed on one ventricle relative to the other so as to produce varying control/decreases in blood ejection from the respective ventricles.

Figure 19:
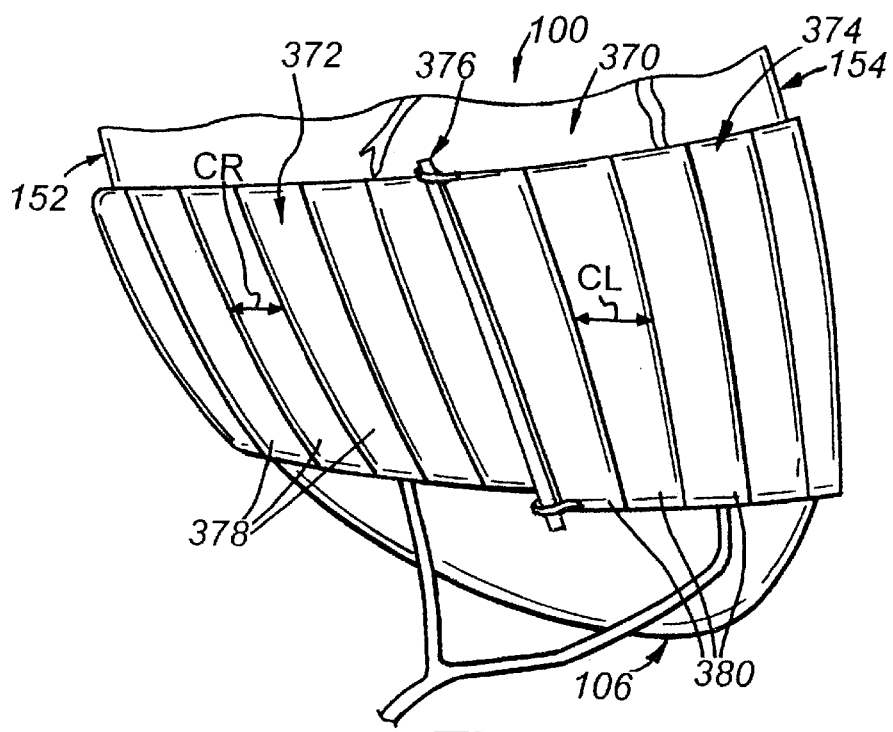
FIG. 19 is a side view of the left and right ventricular region of an affected heart with an applied cardiac wrap having inflation elements of smaller diameter with respect to the right ventricle than with respect to the left ventricle.

Accordingly FIG. 19 depicts a modular contractile wrap 370 having a right section 372 and left section 374 joined together by an exemplary rod and loop connection system 76 as described above. The coverage along the opposing left and right ventricular free wall areas is roughly the same for both wrap sections 372, 374 in this embodiment. In other words, the wrap sections each extend approximately the same width along the ventricular region between the AV groove/heart valve plane and the apex. According to this embodiment, the right section's (372) inflation elements 378 define circumferences/diameters CR that are smaller that the circumferences/diameters CL of the left section's (374) inflation elements 380. This translates into a smaller internal cross-sectional area for the right section's inflation elements 378 than the internal cross-sectional area of the left section's inflation elements 380.

Figure 20:
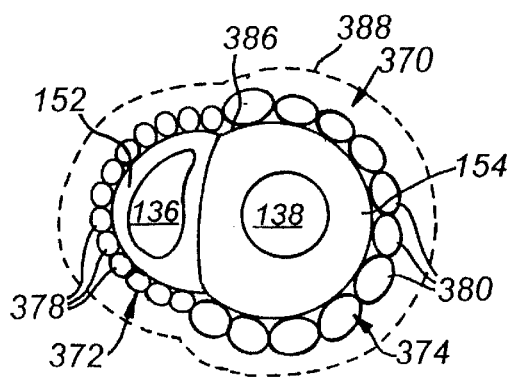
FIG. 20 is a cross section of the heart and cardiac wrap of FIG. 19 comparing end systolic position to end diastolic position.

With further reference to FIG. 20, the wrap 370 is commonly inflated its end systolic position (outline 386) relative to the end diastolic position (dashed outline 388) in which the wrap is largely uninflated. In this embodiment, the effective separation of the left section 374 from the right section due to tissue growth means that the right section is (beneficially) not completely compressed (note more-opened right ventricle 136) because forces generated at the left section are effectively shielded from the right section except for the action at the heart septum, and the lower load pressure at the right section is intentionally offset by the smaller inflation element circumference. The result is that normal left and right ventricular stroke volume are attained.

Figure 21:
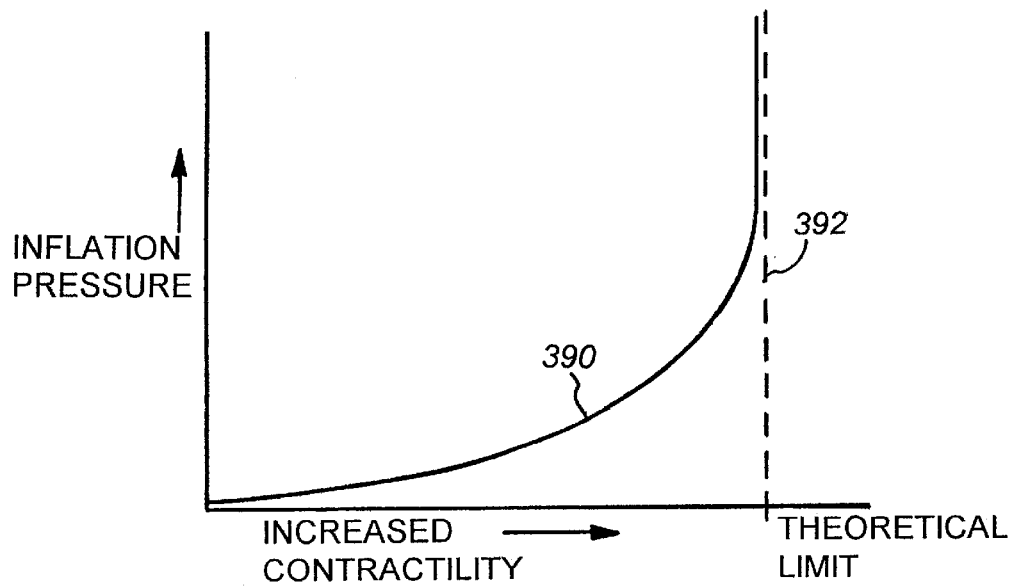
FIG. 21 is a graph of wrap contractility versus inflation element circumference for a given inflation pressure.

With reference to the modular wrap design of FIGS. 19 and 20, a graph of wrap contractility versus inflation element systolic inflation pressure is detailed in FIG. 21. The plotted curve 390 increases asymptotically toward a theoretical contractility limit represented as a dashed vertical line 392. In the case of a single layer design, 36% is the theoretical limit and, in the case of a double layer design, the limit is increased to 62%. This curve assumes roughly equal left and right coverage areas as noted above.

Reduced contractility in one modular wrap section relative to another can also be achieved by introducing "dead space" in the wrap section. Dead space is a region of wrap, which is not active does not provide direct ventricular assistance. For example the non-distensible wall extension 202 in FIG.7 is a dead space that does not actively assist the right ventricle. Note that the use of dead space is effective in both displacement and contractile wrap designs, and is effective mainly after tissue-wrap adhesion is complete.

In general, applying a displacement to one ventricle always has some effect on the opposing ventricle due to the transmission of forces across the heart. For example, a displacement of the wrap against one ventricle may cause the wrap to move away from that ventricle so that it is drawn into compression against the opposing ventricle—where the wrap is relatively unanchored to the wall. Likewise, where the wrap is anchored to the septum or other locations along the heart wall, transmission of displacement to a given ventricle may cause the septum to deform based upon hydraulic action of blood in the ventricle, thereby compressing the opposing ventricle from within. Accordingly in designing a wrap, the size and shape of each side should be chosen taking the "cross-talk" that will occur between ventricles under compression into account.

Figure 22:
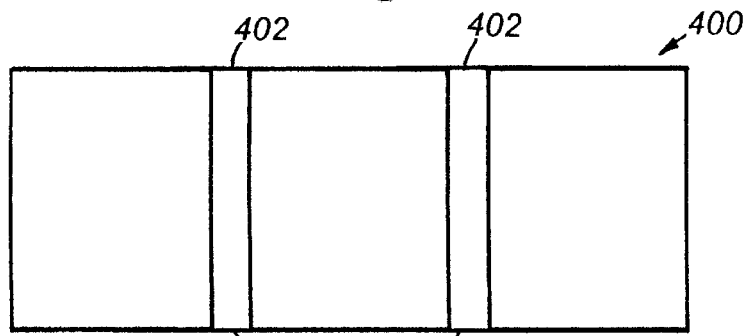
FIGS. 22–24 are partial side views of cardiac wrap sections having various configurations of introduced dead space sections between active ventricular assist regions of the wrap.
Figure 23:
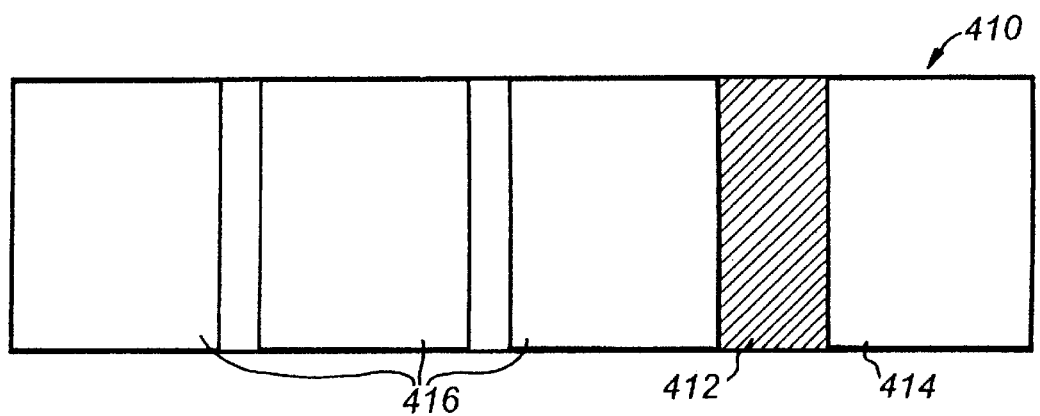
Figure 24:
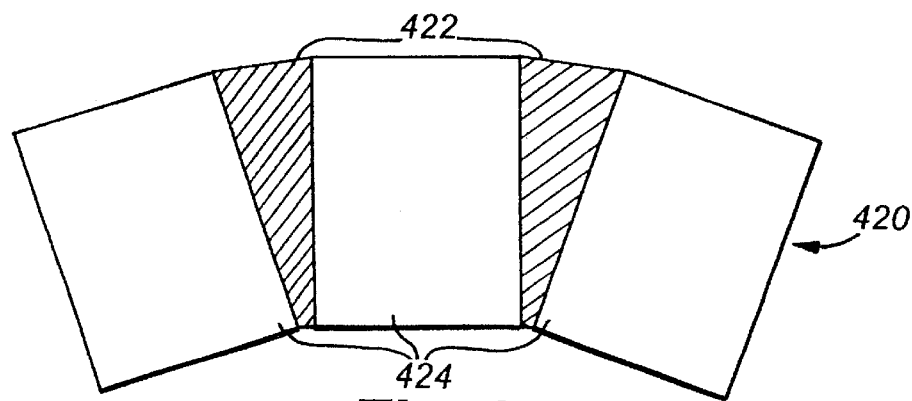

FIG. 22 schematically illustrates a wrap 400 with an application of uniform dead spaces 402 between parallel inflation elements 404. Similarly, FIG. 23 shows a wrap 410 having an axial region of dead space 412 between a single inflation element 414 and a connected group of three elements 416. All elements 414, 416 are parallel. Finally, FIG. 24 shows a wrap 420 having two eccentric (wedge-shaped) regions of dead space 422 disposed between inflation elements 424 that cause the wrap 420 to assume a somewhat actuate shape. This arrangement exemplifies how dead spaces can be employed to improve wrap fit when placed around an affected heart.

A possible concern with modular wrap designs is their inherent complexity. In general, complexity increases as fit improves. It is contemplated that some of the above-described advantages can be provided to a one-piece wrap design without adopting a multi-section modular construction. Fit is generally determined by three parameters—wrap circumference, wrap position with respect to the heart's AV groove and wrap "cone angle." Described further below are balance strategies and techniques that account for these parameters, and do not compromise wrap fit.

Figure 25:
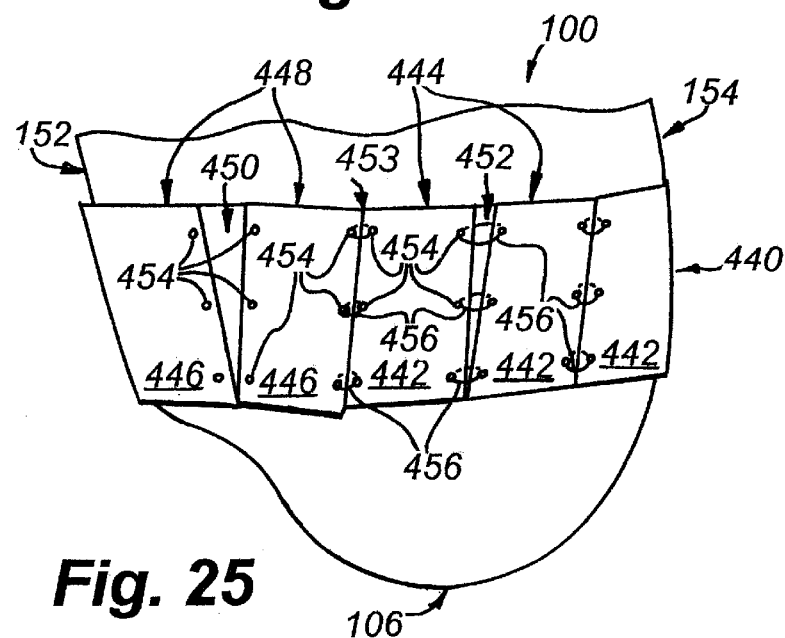
FIG. 25 is a side view of a left and right ventricular region of an affected heart showing ties between sections of a predetermined wrap area to assist in fit and adjustment.

A basic one-piece wrap embodiment is shown in FIG. 25. The depicted wrap 440 is populated by a larger number of inflation elements 442 on the left section 444 than the number of inflation elements 446 on the right section 448. Note the left section can be less-populated than the right according to an alternate embodiment. The dead space 450 between the elements on the less populated section 448 can be used to adjust fit of the wrap 440 with respect to the ventricular region of the heart 100. In general, the dead spaces 450, 452 and 453 between inflation elements can be provided with tie holes through which a sturdy thread or sting or other tie material 454 can be looped (loops 456). By selectively tightening and loosening loops to cinch up selected areas of the dead space, the fit and tautness of the wrap can be finely adjusted. Note that dead space 450 is not clinched, space 452 is partially clinched, and space 453 is fully clinched. Snare knots, snares and other advanced closure/fastening techniques can be employed to complete attachment at the appropriate location. Note that other connection mechanisms and techniques can be used to manipulate the dead spaces to achieve a fit such as that shown in FIG. 25. Also note that dead spaces can be selectively clinched on one portion of the wrap to increase the population of inflation elements on one portion of the ventricular region, while fully deploying dead spaces on another portion can decrease inflation element population.

Figure 26:
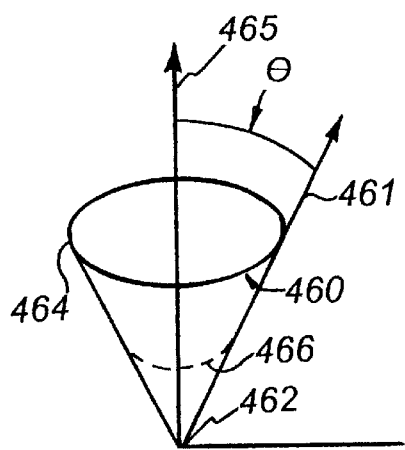
FIG. 26 is a schematic perspective view generally expressing cardiac wrap cone angle.

FIG. 26 schematically depicts the "cone angle," which relates to the opening of the wrap when it is applied around the ventricular region of the heart. The wrap defines a surface geometry that approximates a portion of a cone 460. The cone is defined by an angle $\theta$ that represents the angle of a surface line 461 taken from the remote origin point 462 with respect to a center axis 465 passing through the cone 460. In practice the wrap defines a cone portion extending generally from the top edge 464 to the middle of the cone (dashed line edge 466). Hence the extension of the cone to the origin is an imaginary line for illustrating the measurement of the "cone angle."

Adjustment of cone angle is desirable to ensure proper wrap fit, and to maximize effectiveness of the application of pressure. The dead spaces and associated ties of the wrap 440 (FIG. 25) provide the further advantage of enabling the cone angle of the wrap to be varied along the axis of the heart during implantation so as to optimize fit.

Figure 27:
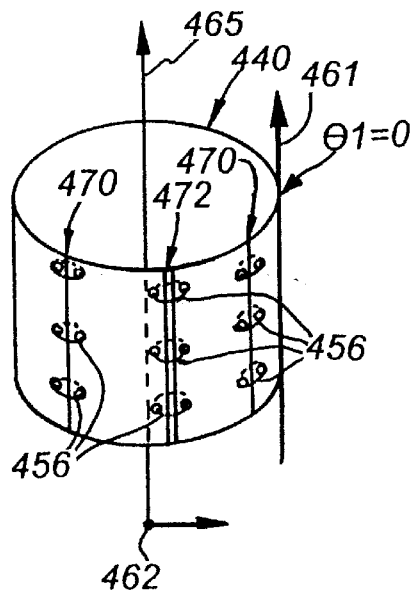
FIGS. 27–29 are schematic perspective views of exemplary cone angles into which the cardiac wrap of FIG. 25 can be adjusted.

FIG. 27 depicts an example of the minimal cone angle configuration for the wrap 440 in which the cone angle $\theta 1$ essentially equals 0 (being parallel to the center axis 565), and the wrap sides approximately define a cylinder. In this embodiment, the ties 456 are arranged so that the dead spaces are variously clinched (dead spaces 470) to fully join inflation elements and, where slack is needed, partially clinched (dead space 472) so the inflation elements are spaced-apart, but essentially parallel.

Figure 28:
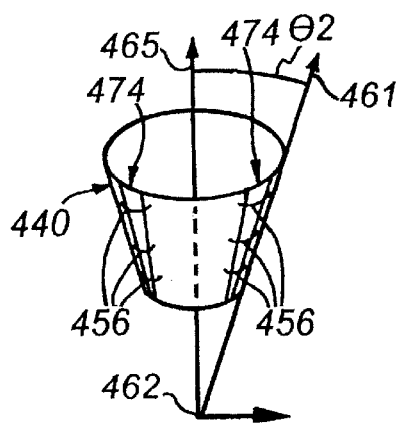

FIG. 28 depicts an example of an intermediate cone angle configuration for the wrap 440 in which the cone angle $\theta 2$ equals a somewhat shallow angle with respect to the axis 465. In this embodiment, the dead spaces 474 are partially clinched by ties 456 so as to define the shallow angle by providing some slack in the lower ties and/or minimal slightly greater slack in upper ties.

Figure 29:
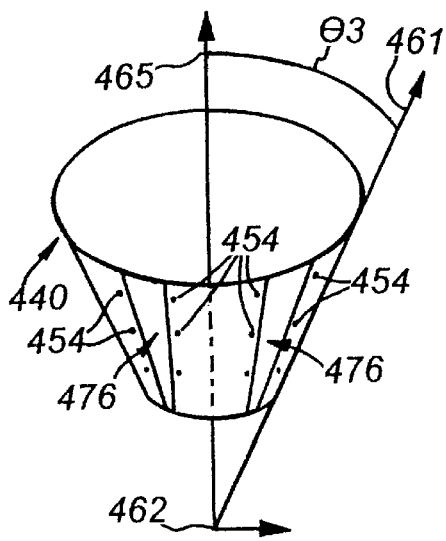

FIG. 29 similarly depicts a maximum cone angle configuration for the wrap 440 in which the cone angle $\theta 3$ equals a greater angle than $\theta 2$, thereby defining a comparatively steeper cone shape. The dead spaces 476 are free of ties, showing only the tie holes 454. Accordingly the wedge-shaped free spaces are fully spread (see, for example the configuration in FIG. 24. Of course, according to an alternate embodiment in which rectangular free spaces are used (see FIG. 22), the maximum cone angle is achieved when the bottom most holes are substantially fully clinched together while the upper holes remain free-forcing the rectangle to assume a wedge shape, bounded on top by the upper rectangular side.

In summary, a force applied on the left side of the wrap is transmitted to the right side, in effect by pushing the heart toward the right side, as this is the backstop against which the force acts absent any significant anchoring of the wrap to the heart. However, if the wrap is fixed along a line on the heart, the pushing force is translated to that fixed line. For example, suturing the wrap along the septal line between the left and right ventricles separates forced applied on the left side from forces applied on the right side. Note that this separation is only partial, since pressures applied to one ventricle are partially transmitted through the interventricular septum.

Figure 30:
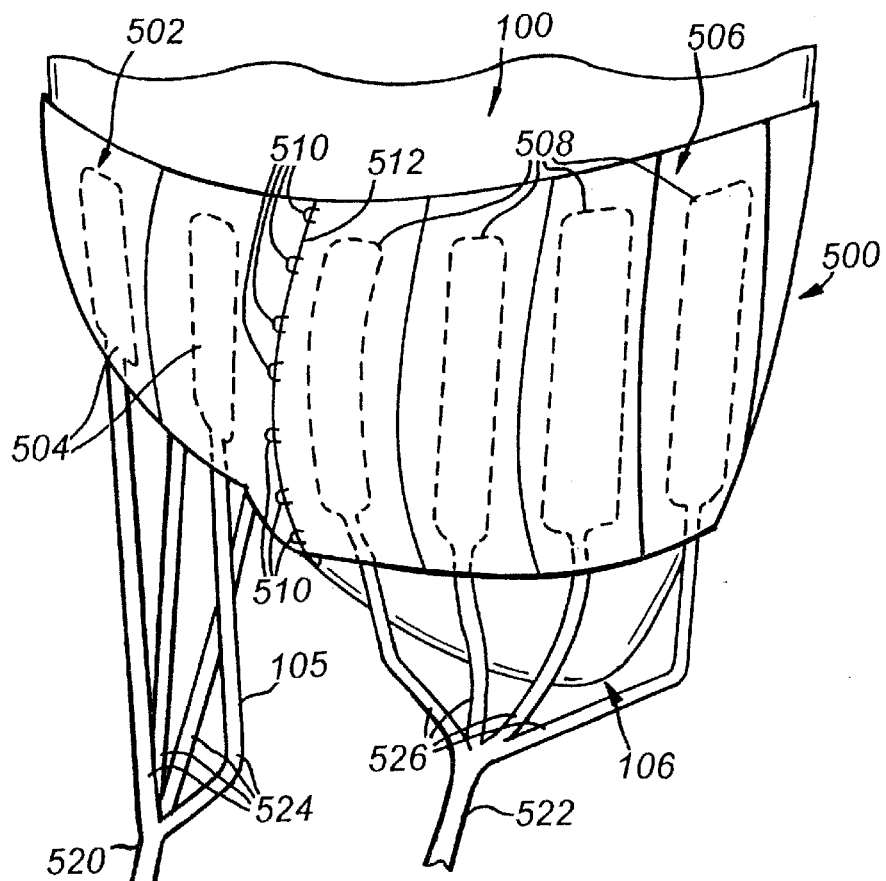
FIG. 30 is an exposed side view of the left and right ventricular regions of a heart with an applied cardiac wrap having separately driven inflation elements for the left and right ventricles.

When the wrap forces are separated by a heart attachment, then it is possible to actuate the left and right ventricles independently. Such a wrap would have independent inflation supplies, one possibly driven at a higher end systolic pressure than the other to control and balance ventricular ejection. A left and right independently driven cardiac wrap system according to an embodiment of this invention is depicted in FIG. 30. The wrap 500 is applied to an affected heart. It includes a right section 502 with a set of parallel right inflation element balloons 504 and a left section 506 with a set of parallel left inflation element balloons 508. The wrap 500 is anchored to the area of the septum using hooks or sutures 510 that extend on a line 512 between the right and left wrap sections 504 and 506, respectively.

Figure 31:
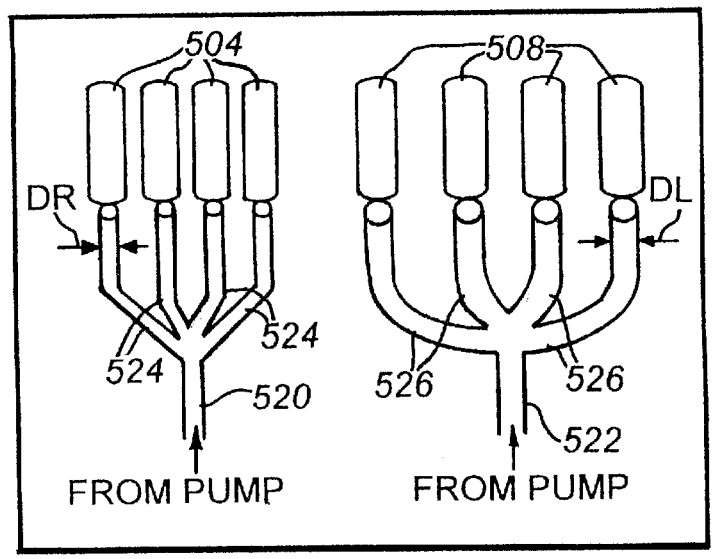
FIG. 31 is a schematic plan view of two sets of branched interconnections for left ventricle and right ventricle inflation with reference to the cardiac wrap of FIG. 30.
Figure 32:
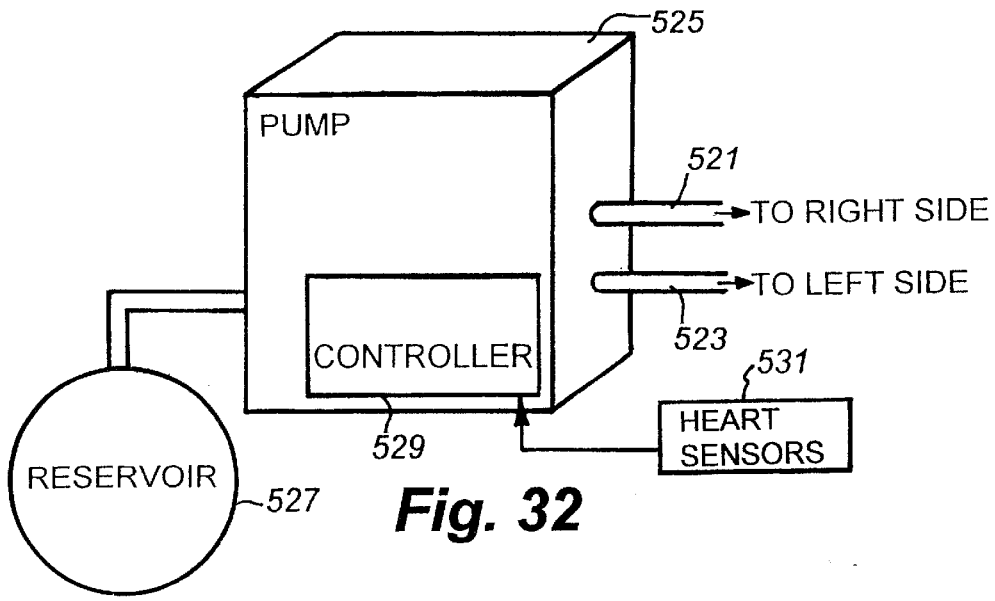
FIG. 32 is a schematic diagram of a pump assembly for use with a pair of separately driven sets of inflation elements.

Referring also to FIG. 31, the inflation elements/balloons (504, 508) of the right and left wrap sides 502, 506 are separately driven through independent right and left feed conduits 520 and 522, respectively. As detailed in FIG. 32, the conduits 520, 522 can be separately interconnected to outputs 521, 523 of a pump 525 and reservoir 527 having a controller 529 that can individually regulate the fluid outputs 521, 523. The right feed conduit 520 branches to individual feed tubes 524 in respective fluid communication with each of the right inflation elements 504. Likewise, the left feed conduit 522 branches to individual feed tubes 526 in respective fluid communication with each of the left inflation elements 508.

By providing right feed tubes 524 each with a smaller cross section/inner diameter DR than the cross section/inner diameter DL of each of the left feed tubes 526, the resistance is increased in the right feed tube set, and the left inflation elements 508 will tend to inflate first. The resistance in the feed tubes represents a pressure drop from main feed conduit pressure to the feed tube pressure. If the difference between load pressures in the right feed tube arrangement and left feed tube arrangement is a constant difference pressure, then adjusting the left feed tube arrangement and right feed tube arrangement to exhibit a similar difference in pressure drops will enhance left and right balance. However, the final pressure in both left and right inflation elements will be constant in the steady is state. However, most cardiac cycles do not allow for application of steady-state pressures. It may also be desirable to reduce the contractility of the right wrap section 502 by adopting smaller inflation elements (504), larger dead space, and the like—depending on the compensative power of the heart. Note that, even when both the left and right wrap sections are driven with the same supply, adjusting the resistances in the right side supply tubes can improve ventricular output balance, particularly following appropriate tissue-wrap adhesion.

The above described embodiment, wherein the left and right wrap sections actuate separately, has an additional advantage in that the left and right sections can be actuated at different times when there are two dedicated independent left and right supplies. The depicted pump 525 (FIG. 32) can include a controller 529. The depicted controller 529 (and other controllers described herein) can receive information from various heart sensors 531 including pacemakers, heart monitors and other electrical sensors that analyze the electrical wave pattern of the heart (e.g. p-wave, s-wave and QRS wave). In addition mechanical sensors (and transducers therefor) can be employed including heart volume sensors applied to the wrap or elsewhere on the heart, and pressure sensors at various locations. These sensors can allow the controller to synchronize pump operation (including the taking-account of expected wrap fill and empty delays) with the pumping action of each ventricle.

The controller 529 and pump 525 can be adapted to trigger the output and with-drawal of fluid from the right output 521 according to a different timing than the left out-put 523. This can be accomplished using valves that interact with the outputs and a pump/vacuum source, or by providing two independently controlled pump/vacuum circuits. In one embodiment, where pulmonary edema is suspected, it can be beneficial to actuate the left wrap section first so as to reduce the pressure in the lungs during subsequent right wrap section actuation. In one embodiment the actuation time of the left ventricle can be approximately 50–100 milliseconds earlier than that of the right.

According to an alternate embodiment here pulmonary edema is of less concern, the right ventricle can be actuated by the pump approximately 50–100 milliseconds earlier than the left ventricle, causing less blood to fill the right ventricle as it is already displaced as the left fills. Again, this mode of operation is effective primarily after a degree of tissue-wrap adhesion has occurred.

According to yet another embodiment, the pump can actuate the left wrap section in synchrony with every cardiac cycle, and the right wrap section in synchrony with every other cardiac cycle. Effectiveness of this mode may again depend upon a degree of tissue-wrap adhesion having occurred.

According to yet another embodiment, the duration of inflation supply in the left wrap section is varied with respect to the right section, whereby the left section and right section are supplied at the same pressure, but the pressurized condition is maintained in the right section for a duration shorter than in the left section (approximately 100 milliseconds shorter for example). This mode again contemplates tissue-wrap adhesion for maximum effectiveness. It is contemplated that a device configured for left/right separation can be adjusted along these parameters to suit a patient's varying condition of health.

Figure 33:
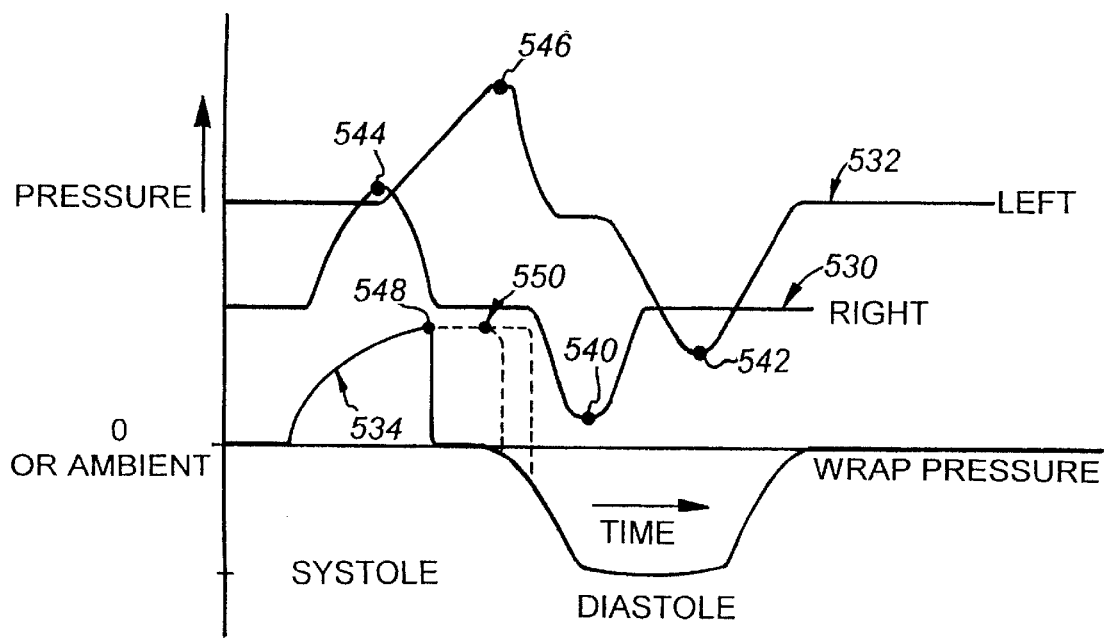
FIG. 33 is a graph of left and right ventricular pressures with respect to wrap pressure for a systole/diastole cycle.

According to an alternate embodiment, a wrap design in which the right and left halves are not separately controls—and which therefore tends to produce more right ventricular output than left ventricular output—can be compensated by increasing the actuation time to, in essence hold systole for a longer duration with respect to the heart's natural rhythm. Referring to the graph of FIG. 33, the ventricular pressures in the right and left ventricles (plots 530 and 532, respectively) are plotted with respect to wrap pressure (plot 534). When the pressure in the wrap is less than 0 (or ambient pressure) there is no force applied to the heart. The heart cycles through a period of filling indicated by lower ventricular pressure (graph points 540, 542) and a period of ejection indicated by higher ventricular pressures (graph points 544, 546). Wrap inflation that matches pressures in the heart is present at point 548. Delaying the deflation of the wrap increases the duration of forces applied to the heart as represented by the extended dashed line 550. In one embodiment the delay before deflation is approximately 100 milliseconds. This can increase the total cycle from inflation to deflation from approximately 200 milliseconds to approximately 300 milliseconds. In the case where the right ventricle empties first under assistance, the left ventricle will also fully empty provided that the pressure applied to the left ventricle exceeds the afterload at the end of wrap actuation. Since pressure applied to the heart rises with time, picking a drive pressure higher than the left ventricular after load pressure and increasing the inflation duration provides time for the inflation elements to reach this elevated pressure, and thus eject the left ventricle. In this example (generally with full coverage of the ventricles) both the right and left ventricles are completely emptied, which is an unnatural condition, but can be tolerated in some situations. This strategy can be particularly effective when the assistance is applied every other cardiac cycle, as described above.

According to an alternate embodiment, a cardiac wrap can be constructed with a textured surface to encourage growth between the heart and device, effectively separating left and right actuation. Assistance applied to the right side can be reduced during the time of implantation in response to the condition of the patient. This is accomplished by obstructing inflation supply to one or more inflation elements on the wrap side where assistance in desired, to be less—typically the right section. To obstruct fluid flow to one or more inflation elements the surgeon can clamp, or by other means, obstruct flow to an inflation element while the wrap is evacuated. This effectively renders the obstructed element as dead space. This partially obstructed wrap condition generates reduced contractility in the right section, resulting in less ejection from the right ventricle than would have occurred if the particular inflation element were operational.

According to another embodiment, an inflation element can be filled by injection of a biocompatible substance thereinto—preferably a solid substance that seals the injection site. The act of filling an inflation element (1) serves to decrease the circumference of the wrap in contractile wraps, or (2) applies force to the surface of the heart (in displacement wraps. The filling would also, as described above, render the filled inflation element as dead space. The filling may be preferred to occlusion/obstruction of the element because it affords the surgeon the additional opportunity to fit or tighten the wrap about the heart.

The heart is roughly conical in shape. The largest blood volume per unit axial length is found near the base of the heart. Therefore, placement of the wrap as close to the ventricular valve plane as possible generally improves assistance, and consequently improves heart stroke volume. This principle can be used to balance left and right output from the heart. Placing the wrap higher on the left side than the right side with respect to the valve plane has the effect of decreasing assistance to the right side relative to the left. The effect is to achieve the same result with wraps containing shorter inflation elements in the right section relative to the left section, while maintaining inflation element symmetry in the wrap. This application technique can be termed "eccentric placement" of the wrap since the wrap's central axis and the heart's central axis are non-parallel.

According to another embodiment, the cardiac wrap design can be configured as either pure displacement or pseudo-contractile. Displacement wraps create heart contraction by displacing the ventricular free wall a unit volume when a unit of volume is introduced into the wrap. Contractile wraps can create larger than unit volume displacements of the ventricular free wall when a unit of volume is introduced into the wrap. These wrap designs, like those described above, typically do not separate left and right ventricular actuation.

Figure 34:
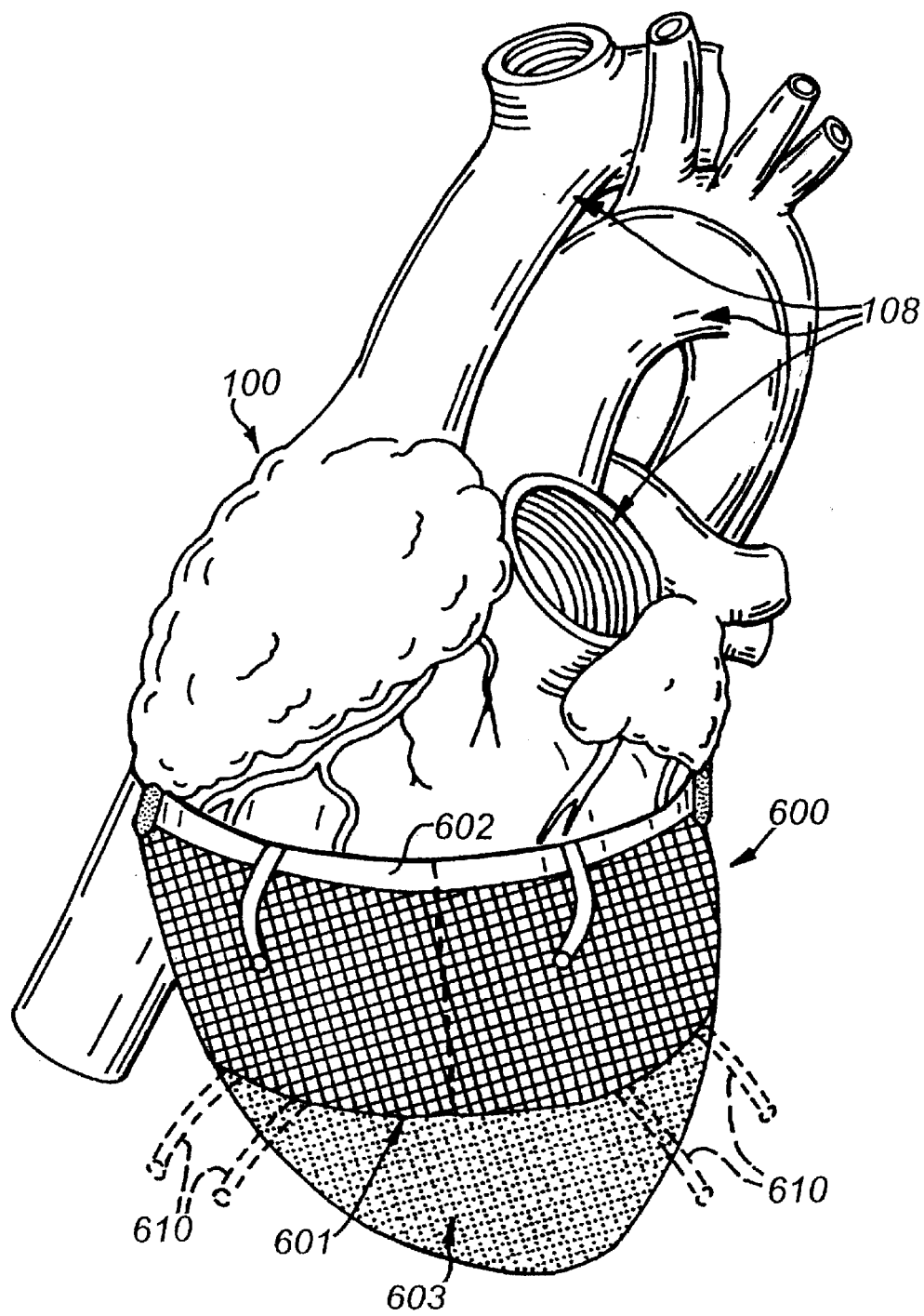
FIG. 34 is a perspective view of an affected heart having an applied cardiac wrap according to an alternate embodiment of this invention.

FIG. 34 details a wrap 600 applied to the ventricular region of the affected heart 100. The wrap 600 comprises a mesh or net material constructed from a biocompatible material that is flexible, but non-distensible. The net extends generally around the mid-riff of the ventricular region, but can be variably placed in accordance with the description herein. The net can be connected at its lower edge 601 to a lower apical covering 603 of appropriate biocompatible material to prevent dilation in a manner described generally with reference to FIG. 8. This mesh is designed for short-term attachment due to the possible build-up of biological growth. An alternate material that is less prone to build-up can be used in an alternate application. The exemplary wrap includes an elastic band to be located adjacent the AV groove region. However a variety of temporary and permanent attachment mechanisms can be employed.

Figure 36:
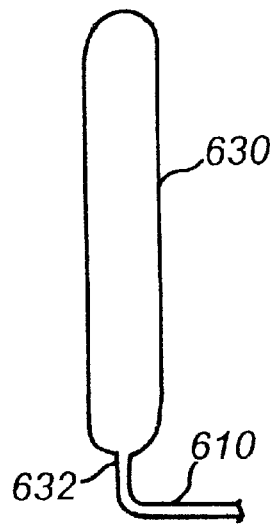
FIG. 36 is a side view of a cardiac wrap inflation element and associated fluid conduit interconnection according to an embodiment of this invention.
Figure 37:
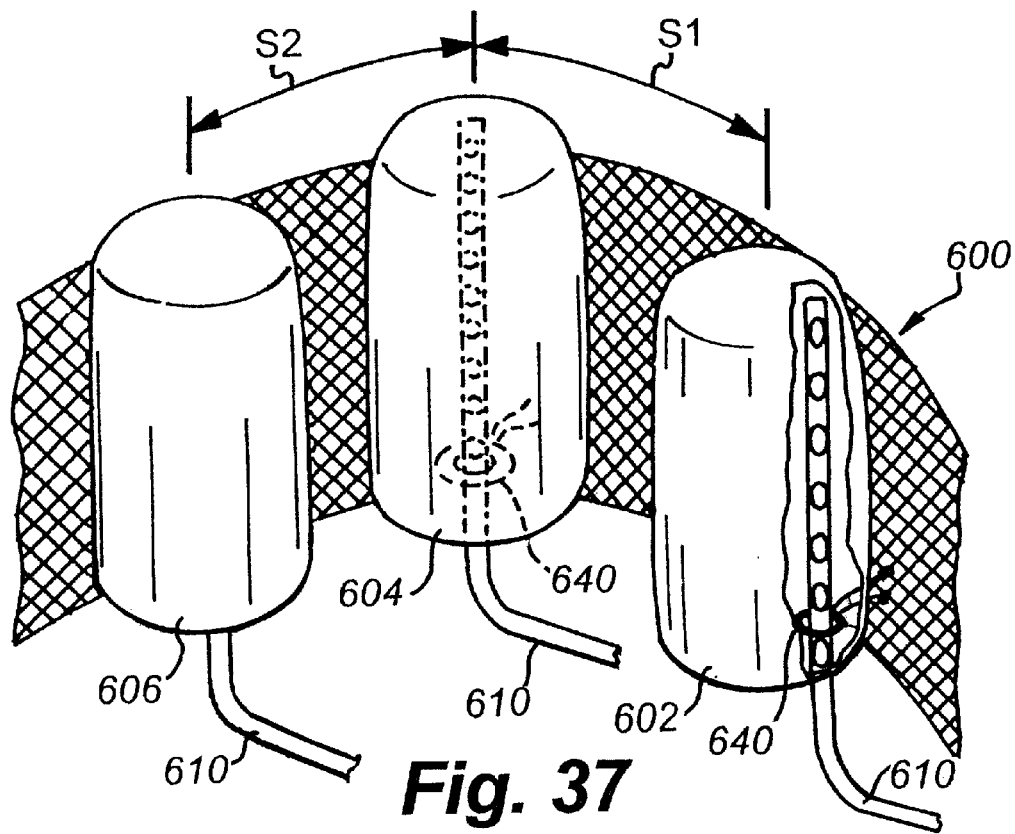
FIG. 37 is aft exposed fragmentary perspective view of a portion of a cardiac wrap of FIG. 34 and attached inflation elements.

Referring further to FIG. 37, a portion of the interior of the wrap 600 is shown in further detail. The interior of the wrap encloses a plurality of inflation elements, herein comprising balloons 602, 604 and 606 of a type generally described above. These balloons are fed by fluid feed tubes 610. The tubes are shown in phantom in FIG. 34 extending from points on the lower portion of the wrap 600. The feed tubes 610 can be connected to feed the balloons according to various alternate embodiments. Two such connections are depicted in FIGS. 35 and 36.

Figure 35:
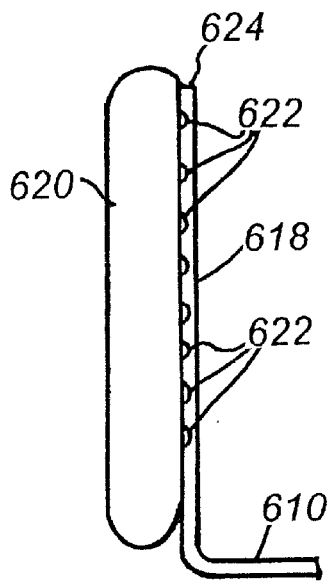
FIG. 35 is a side view of a cardiac wrap inflation element and associated fluid conduit interconnection according to an embodiment of this invention.

In FIG. 35, the terminal end 618 of the feed tube 610 is adhered along the length of an exemplary balloon 620. A series of ports 622 are defined along the tube end 618. These ports 622 are joined to corresponding openings in the balloon 620. Appropriate cement, sealer, or specialized molding processes can be used to create the interconnection between the tube end and the balloons. The top 624 of the tube end is sealed.

In FIG. 36 an exemplary balloon 630 is fed by the terminal end 632 of a feed tube at its end (bottom). A single interconnection is made between the tube end and the balloon 630. The cross section of the tube should be sufficient to enable rapid inflation/deflation of the balloon at a given pressure and flow rate. The tube end can be cemented, welded, fitted or otherwise adhered to the balloon using a variety of conventional joining techniques.

Referring again to FIG. 37, the wrap encloses a series of parallel balloons 602, 604, 606. These balloons can be provided separately from the mesh wrap prior to implantation. Accordingly, the balloons are adapted to be joined to the wrap in a predetermined number and spacing depending upon the particular condition of the affected heart. For example, the spacing SI between balloons 602 and 604 can be greater than the adjacent spacing between balloons 604 and 606. A closer spacing pattern can be implemented where more balloons are desired in a given area (e.g. the left ventricular region). Likewise, a greater spacing can be employed where fewer balloons are desired (e.g. the right ventricular region. The balloons are secured to the mesh according to a number of techniques. As shown herein, the base ends of the feed tubes 610 are tied by loops 640 to the mesh. Additional anchor points can be formed on the balloons to stabilize them where appropriate.

It should be clear that an advantage of the wrap 600 is that inflation elements can be selectively applied to locations where displacement is particularly desired, while other locations where reduced inflation is needed can be provided with fewer or no inflation elements.

Figure 38:
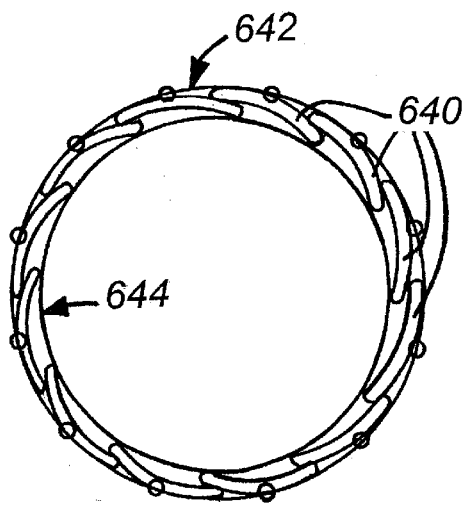
FIGS. 38 and 39 are somewhat schematic cross sections of a heart with the cardiac wrap of FIG. 34 applied, showing overlapping/contacting inflation elements in diastole and systole, respectively.
Figure 39:
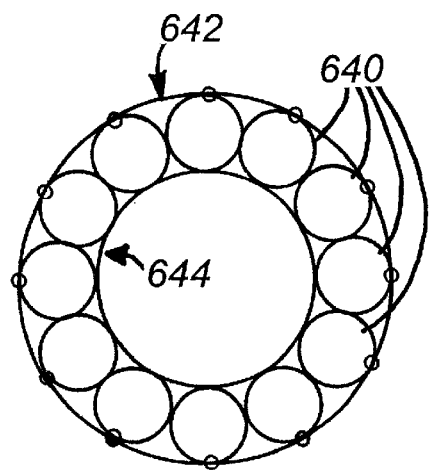
Figure 40:
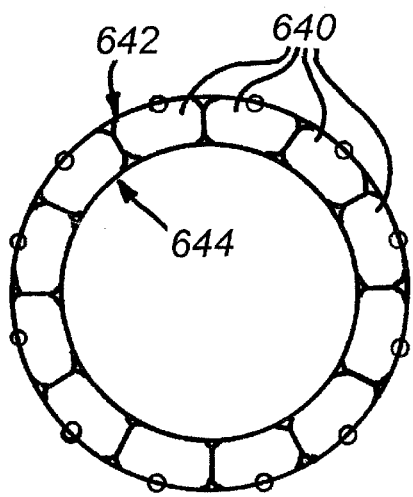
FIG. 40 is a somewhat schematic cross section of the heart with the cardiac wrap of FIG. 34 applied, showing overlapping/contacting inflation elements partially inflated, in either mid-diastole or mid-systole.

FIG. 38 schematically details a basic wrap arrangement in which inflation elements/balloons 640 are attached to the mesh outer covering 642 of the wrap. The diastolic ventricular volume 644 is surrounded by the balloons. The balloons in this example overlap. This arrangement produces the systolic ventricular shape shown in FIG. 39 in full compression. Note that the balloons 640 are in contact with each other. This miti-gates a potential risk of biological growth within the open interior of the wrap according to this embodiment, since the volume within the wrap enclosure 642 is more fully occupied at all times. FIG. 40 shows that the overlapping balloons fully occupy the space between the wrap enclosure 642 and ventricular volume 644 at mid-systole or mid-diastole. Note that arrangement of FIG. 40 can also be achieved at full systole using oversized, over-lapping balloons.

Figure 41:
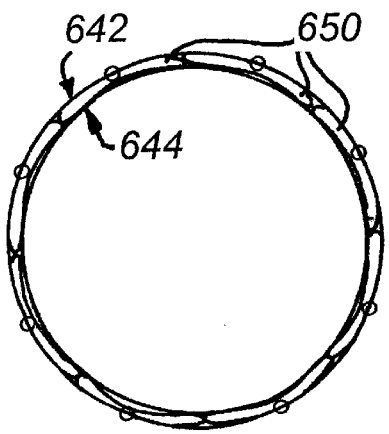
FIGS. 41 and 42 are somewhat schematic cross sections of the heart with the cardiac wrap of FIG. 34 applied, showing non-overlapping/non-contacting inflation elements in diastole and systole, respectively.
Figure 42:
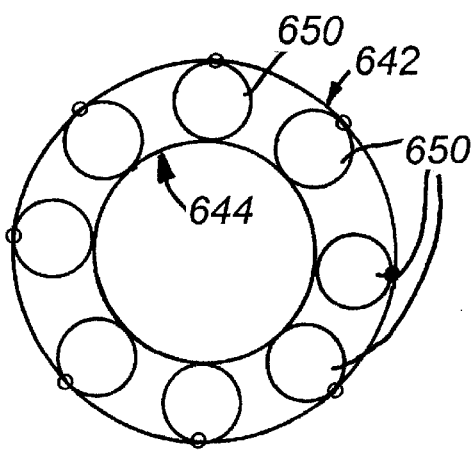
Figure 43:
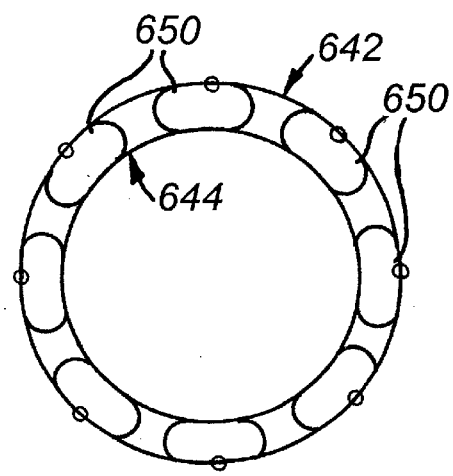
FIG. 43 is a somewhat schematic cross section of the heart with the cardiac wrap of FIG. 34 applied, showing non-overlapping/non-contacting inflation elements partially inflated, in either mid-diastole or mid-systole.

FIG. 41 schematically details another basic wrap arrangement in which inflation elements/balloons 650 are attached to the mesh outer covering 642 of the wrap. The diastolic ventricular volume 644 is surrounded by the balloons. The balloons in this example are either barely contacting or non-contacting. This arrangement produces the systolic ventricular shape shown in FIG. 42 in full compression. Note that the balloons 650 are out of contact with each other at full inflation. This arrangement may be preferred where reduced assist is desired. FIG. 43 shows the non-contacting balloons 650 at mid-systole or mid-diastole.

Figure 44:
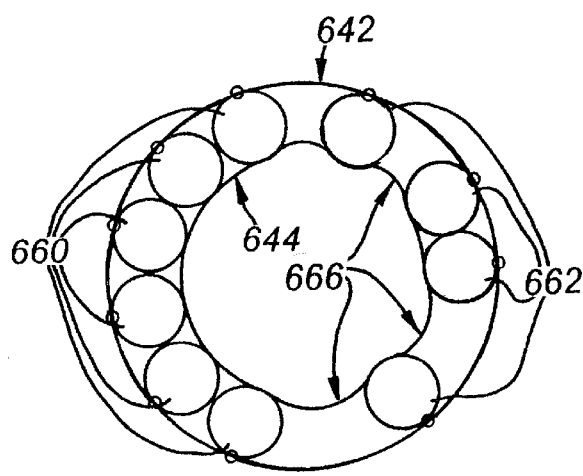
FIG. 44 is a somewhat schematic cross section of the heart with the cardiac wrap of FIG. 34 applied, showing a combination of overlapping/contacting and non-overlapping/non-contacting inflation elements in systole.

It is expressly contemplated that the overlapping and spaced-apart arrangements can be combined in varying degrees to produce a wrap. For example, FIG. 44 shows an arrangement in which one set of balloons 660 is essentially overlapping and contacting in systole, while another set of balloons 662 is largely non-overlapping and non-contacting in systole. The compression pattern of the ventricular volume 644 is irregular, having less-compressed regions 666 in the areas between non-contacting balloons. The spacings and overlap between balloons can be varied around the circumference for a unique assist pattern customized to the affected heart's needs.

The foregoing has been a detailed description of embodiments of the invention. Various modifications and additions can be made without departing from the spirit and scope of the invention. For example, the various embodiments described herein can be combined in whole or in part to produce a number of modified cardiac wrap designs possessing features of a number of different wrap designs. The inflation elements used herein can be constructed in a variety of shapes including cones, cylinders, crescents or spheres depending upon the desired displacement effect sought. The number of material layers used in the wrap can be varied and more, or fewer, than two layers can be employed where appropriate. Also, while several illustrated embodiments specify a tissue-wrap adhesion that is generally based upon natural tissue growth processes, it is contemplated that all, or portions, of a wrap may be anchored to the adjacent heart wall using mechanical fasteners, sutures, adhesives and the like that can strengthen the bond and support the interconnection between the heart wall and wrap until natural growth can occur. Accordingly, this description is meant to be taken only by way of example, and not to otherwise limit the scope of the invention.

What is claimed is:

1. A flow-balanced cardiac wrap that encloses a ventricular region of a heart comprising:
   a first section that applies a first variable assist force to the left ventricular region; and
   a second section that applies a second variable assist force to the right ventricular region;
   wherein the first section applies the first variable assist force over a first area on the left ventricular region and the second section applies the second variable assist force over a second area on the right ventricular region and wherein the second area is smaller than the first area.

2. The flow-balanced cardiac wrap as set forth in claim 1 wherein the second area is located closer to an apex of the heart than the first area.

3. A flow-balanced cardiac wrap that encloses a ventricular region of a heart comprising:
   a first section that applies a first variable assist force to the left ventricular region; and
   a second section that applies a second variable assist force to the right ventricular region;
   wherein the first section applies the first variable assist force over a first area on the left ventricular region and the second section applies the second variable assist force over a second area on the right ventricular region and wherein the second area is located closer to an apex of the heart than the first area.

4. A flow-balanced cardiac wrap that encloses a ventricular region of a heart comprising:
   a first section that applies a first variable assist force to the left ventricular region;
   a second section that applies a second variable assist force to the right ventricular region; and
   a pump for directing inflation pressure to each of the first section and the second section, the pump including a controller that causes the first section to apply the first assist force at a first time and the second section to apply the second assist force at a second time, the first time being different from the second time.

5. The flow-balanced cardiac wrap as set forth in claim 4 wherein the second time begins at a predetermined time after the first time begins.

6. A flow-balanced cardiac wrap that encloses a ventricular region of a heart comprising:
   a first section that applies a first variable assist force to the left ventricular region; and
   a second section that applies a second variable assist force to the right ventricular region;
   wherein each of the first section and the second section include inflation elements, the inflation elements of the first section each being larger in volume at a predetermined inflation pressure than the inflation elements of the second section at the predetermined inflation pressure.

7. A flow-balanced cardiac wrap that encloses a ventricular region of a heart comprising:
   a first section that applies a first variable assist force to the left ventricular region; and
   a second section that applies a second variable assist force to the right ventricular region;
   wherein each of the first section and the second section include inflation elements, a number of inflation elements in the first section each being greater than a number of inflation elements in the second section.

8. A flow-balanced cardiac wrap that encloses a ventricular region of a heart comprising:
   a first section that applies a first variable assist force to the left ventricular region; and
   a second section that applies a second variable assist force to the right ventricular region;
   wherein each of the first section and the second section include inflation elements, the inflation elements in the second section having dead spaces therebetween that are non-distensible.

9. A flow-balanced cardiac wrap that encloses a ventricular region of a heart comprising:
   a first section that applies a first variable assist force to the left ventricular region; and
   a second section that applies a second variable assist force to the right ventricular region;
   wherein each of the first section and the second section include inflation elements, the inflation elements of the first section extending from a top wrap edge to a first bottom edge in a direction toward an apex of the heart for a first distance, the inflation elements of the second section extending from the top wrap edge to a second bottom edge in a direction toward the apex for a second distance, the first distance being greater than the second distance and a first non-distensible member being attached to the second bottom edge to cover a portion of the right ventricle adjacent to the apex.

10. The flow-balanced cardiac wrap as set forth in claim 9 further comprising a second non-distensible member attached to the first non-distensible member and the first bottom edge, the second non-distensible member covering the apex.

11. A flow-balanced cardiac wrap that encloses a ventricular region of a heart comprising:
    a first section that applies a first variable assist force to the left ventricular region; and
    a second section that applies a second variable assist force to the right ventricular region;
    wherein the second section and the first section are joined at attachment locations, the attachment locations including interconnection elements for variably positioning the second section with respect to the first section.

12. The flow-balanced cardiac wrap as set forth in claim 11 wherein the interconnecting elements are adapted to allow the first section to be attached at a variable angle with respect to the first section, whereby a cone angle of the wrap on the heart is adjustable.

13. The flow-balanced cardiac wrap as set forth in claim 12 wherein the interconnecting elements include one of either interengaging hooks and loops, interengaging ties and interengaging rods and loops located on opposing free ends of the first section and the second section, respectively.

14. A flow-balanced cardiac wrap that encloses a ventricular region of a heart comprising:

a first section that applies a first variable assist force to the left ventricular region; and a second section that applies a second variable assist force to the right ventricular region;

wherein the first section and the second section include a plurality of inflation elements for applying pressure and at least one pair of inflation elements being connected to opposing sides non-distensible dead space, the dead space being adapted to be clinched together to vary a spacing distance and angle between each of the pair of inflation elements.

15. The flow-balanced cardiac wrap as set forth in claim 14 wherein the dead space includes locations for a plurality of ties, adapted to enable the dead space to be clinched into a plurality of shapes.

16. The flow-balanced cardiac wrap as set forth in claim 14 wherein the dead space defines one of either a wedge shape and a rectangular shape in an non-clinched orientation.

17. A flow-balanced cardiac wrap that encloses a ventricular region of a heart comprising:

a first section that applies a first variable assist force to the left ventricular region; and a second section that applies a second variable assist force to the right ventricular region;

wherein the left section and the right section each include inflation elements to apply the first variable assist force to the left ventricular region and the second variable assist force to the right ventricular region, respectively, and wherein the inflation elements in the right section are sized and arranged to apply a displacement force that displaces a middle portion of the right ventricular region so as to divide blood in a left ventricle of the heart into an ejected portion directed out of the ventricle and a retained portion that remains in the ventricle after application of the second variable assist force.

18. A method for providing cardiac assistance with a cardiac wrap that engages an affected heart comprising:

engaging a ventricular region of the heart with a wrap having a first section and a second section;

applying a first variable assist force to the left ventricular region with the first section; and applying a second variable assist force to the right ventricular region with the second section;

wherein the step of applying the second variable assist force includes applying the second variable assist force to an area of the right ventricular region that is less than an area of the left ventricular region to which the first variable assist force is applied.

19. The method as set forth in claim 18 wherein the step of applying the second variable assist force includes positioning the second section a predetermined location along the right ventricular region so as to compress a right ventricle of the heart into a portion that ejects a stored portion of blood therein and a portion that retains a stored portion of the blood therein upon application of the second variable assist force.

20. A method for providing cardiac assistance with a cardiac wrap that engages an affected heart comprising:

engaging a ventricular region of the heart with a wrap having a first section and a second section;

applying a first variable assist force to the left ventricular region with the first section; and applying a second variable assist force to the right ventricular region with the second section;

wherein the first variable assist force applies a different magnitude of pressure than a magnitude of pressure applied by the second variable assist force.

21. A method for providing cardiac assistance with a cardiac wrap that engages an affected heart comprising:

engaging a ventricular region of the heart with a wrap having a first section and a second section;

applying a first variable assist force to the left ventricular region with the first section; and applying a second variable assist force to the right ventricular region with the second section;

wherein the first variable assist force is applied at a time different than an application of the second variable assist force.

22. A method for providing cardiac assistance with a cardiac wrap that engages an affected heart comprising:

engaging a ventricular region of the heart with a wrap having a first section and a second section;

applying a first variable assist force to the left ventricular region with the first section; and applying a second variable assist force to the right ventricular region with the second section;

wherein the step of engaging includes adjusting a cone angle of the wrap so as to fit the ventricular region in a predetermined orientation.

23. The method as set forth in claim 22 wherein the step of adjusting includes cinching predetermined dead spaces between inflation elements that apply at least one of the first variable assist force and the second variable assist force.

24. A method for providing cardiac assistance with a cardiac wrap that engages an affected heart comprising:

engaging a ventricular region of the heart with a wrap having a first section and a second section;

applying a first variable assist force to the left ventricular region with the first section and applying a second variable assist force to the right ventricular region with the second section;

wherein the step of engaging includes providing inflation elements in each of the first section and the second section that respectively apply the first variable assist force and the second variable assist force, and the step of providing includes sizing the inflation elements in the first section larger than the inflation elements in the second section.

25. The method as set forth in claim 24 wherein the wrap includes a bottom edge that is closer to an apex of the heart on the first section than on the second section and further comprising restraining a portion of the right ventricular region between the apex and the bottom edge adjacent to the second section with a non-distensible member.

26. A method for providing cardiac assistance with a cardiac wrap that engages an affected heart comprising:

engaging a ventricular region of the heart with a wrap having a first section and a second section;

applying a first variable assist force to the left ventricular region with the first section; and applying a second variable assist force to the right ventricular region with the second section;

wherein the step of engaging includes providing inflation elements in each of the first section and the second section that respectively apply the first variable assist force and the second variable assist force; the method further comprising inflating the inflation elements in the first section at a first time and inflating the inflation elements in the second section at a second time, wherein the first time is different from the second time.

27. The method as set froth in claim 26 wherein the first time is relative to each heart blood-pumping cycle and the second time is relative to each other heart blood-pumping cycle, whereby the second time occurs every two first times.

28. The method as set forth in claim 27 wherein the first time initiates before the second time.

29. A flow-balanced cardiac wrap for assisting a ventricular region of an affected heart comprising:

a first section having a first set of inflation elements that variably displace a left ventricular region of the heart over a first area;

a second section having a second set of inflation elements that variably displace a right ventricular region of the heart over a second area; and wherein the first area is greater than the second area.

30. A flow-balanced cardiac wrap as set forth in claim 29 wherein the second area is located so that displacement of the right ventricular region by the second set of inflation elements causes a right ventricle of the heart to eject a portion of blood in the ventricle above the second area and retain a portion of blood in the ventricle below the second area.

31. A flow-balanced cardiac wrap for assisting a ventricular region of an affected heart comprising:

a first section having a first set of inflation elements that variably displace a left ventricular region of the heart over a first area;

a second section having a second set of inflation elements that variably displace a right ventricular region of the heart over a second area; and at least one dead space located between predetermined of the inflation elements on the second section so as to reduce displacement of the right ventricular region.

32. A flow-balanced cardiac wrap for assisting a ventricular region of an affected heart comprising:

a first section having a first set of inflation elements that variably displace a left ventricular region of the heart over a first area, each of the inflation elements of the first set defining a first internal cross-sectional area;

a second section having a second set of inflation elements that variably displace a right ventricular region of the heart over a second area, each of the inflation elements of the second set defining a second internal cross-sectional area; and the first internal cross-sectional area is greater than the second internal cross-sectional area.

33. A flow-balanced cardiac wrap for assisting a ventricular region of an affected heart comprising:

a wrap body having a plurality of parallel inflation elements for displacing the ventricular region to assist the ventricular region; and a plurality of non-distensible dead spaces between predetermined of the plurality of inflation elements, the dead spaces being adapted to be clinched together to define a plurality of shapes for the respective of the dead spaces and spacings between inflation elements adjacent the respective of the dead spaces, whereby fit of the wrap body to the ventricular region can be adjusted by cinching the dead spaces.

34. A flow-balanced cardiac wrap for assisting a ventricular region of an affected heart comprising:

a first section having a first set of inflation elements that variably displace a left ventricular region of the heart over a first area;

a second section having a second set of inflation elements that variably displace a right ventricular region of the heart over a second area; and a first connector set on each of a pair of free ends of the first section and second connector set on each of a pair of free ends of the second section, the first connector set being adapted to interconnect with the second connector set at each of the free ends at a plurality of positions therebetween so as to enable a plurality of discrete configurations for the second section with respect to the first section.

35. The flow-balanced cardiac wrap as set forth in claim 34 wherein the first connector set comprises a first number of connectors at a predetermined spacing therebetween and the second connector set comprises a second number of connectors at the predetermined spacing therebetween and wherein the second number is less than the first number.

36. The flow-balanced cardiac wrap as set forth in claim 35 wherein the first connector set comprises one of hooks and loops and the second connector set comprises one of interengaging loops and hooks, respectively.

37. The flow-balanced cardiac wrap as set forth in claim 35 wherein the first connector set and the second connector set each comprise ties.

\* \* \* \* \*